(12) United States Patent
Tosato et al.

(10) Patent No.: US 7,812,117 B2
(45) Date of Patent: Oct. 12, 2010

(54) VASOSTATIN AS MARROW PROTECTANT

(75) Inventors: Giovanna Tosato, Bethesda, MD (US); Sandra E. Pike, North Bethesda, MD (US); Lei Yao, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 17 days.

(21) Appl. No.: 12/198,810

(22) Filed: Aug. 26, 2008

(65) Prior Publication Data

US 2009/0149380 A1    Jun. 11, 2009

Related U.S. Application Data

(60) Division of application No. 10/405,588, filed on Apr. 1, 2003, now Pat. No. 7,432,236, which is a division of application No. 09/828,000, filed on Apr. 6, 2001, now Pat. No. 6,596,690, which is a continuation-in-part of application No. PCT/US99/23240, filed on Oct. 5, 1999.

(60) Provisional application No. 60/103,438, filed on Oct. 6, 1998.

(51) Int. Cl.
    *C07K 5/00*     (2006.01)
(52) U.S. Cl. .......................... 530/300; 514/2
(58) Field of Classification Search ........................ None
     See application file for complete search history.

(56) References Cited

U.S. PATENT DOCUMENTS

| 5,192,744 A | 3/1993 | Bouck et al. |
| 5,426,097 A | 6/1995 | Stern et al. |
| 5,591,716 A | 1/1997 | Siebert et al. |
| 5,712,291 A | 1/1998 | D'Amato |
| 5,733,876 A | 3/1998 | O'Reilly et al. |
| 5,776,704 A | 7/1998 | O'Reilly et al. |
| 5,854,202 A | 12/1998 | Dedhar |
| 5,872,234 A | 2/1999 | Bandman et al. |

FOREIGN PATENT DOCUMENTS

| CA | 2140814 | 7/1996 |
| WO | WO 96/23001 | 8/1996 |
| WO | WO 96/36643 | 11/1996 |
| WO | WO 98/48003 | 10/1998 |

OTHER PUBLICATIONS

Atreya et al., 1995 Jun;69(6):3848-51.*
Atreya et al., *Journal of Virology*, pp. 3848-3851 (1995).
Bowie et al., *Science* 247:1306-1310 (1990).
Burgess et al., *J. of Cell. Bio.* 111:2129-2138 (1990).
Cho et al., *Eur. J. Biochem.* 266:878-885 (1999).
Coppolino et al., *The International Journal of Biochemistry & Cell Biology* 32:171-188 (2000).
Lazar et al., *Molecular and Cellular Biology* 8:1247-1252 (1988).
McDonnell et al., *The Journal of Biological Chemistry* 271(14):7891-7894 (1996).
Michalak et al., *Biochem. J.* 285:681-692 (1992).
Patton et al., *The Journal of Biological Chemistry* 270(36):21404-21410 (1995).
Pike et al., *Blood* 94(9): 2461-2468 (1999).
Pozzan et al., *Physiological Reviews* 74(3):595-602 (1994).
Prasad et al., *Electrophoresis* 20:1065-1074 (1999).
Ramsamooj et al., *Cancer Research* 55:3016-3021 (1995).

* cited by examiner

*Primary Examiner*—Misook Yu
(74) *Attorney, Agent, or Firm*—Klarquist Sparkman, LLP

(57) ABSTRACT

Specific fragments of vasostatin are disclosed. These fragments are of use in methods of stimulating the proliferation or survival of a hematopoietic cell exposed to a chemotherapeutic agent or irradiation. Methods of stimulating the proliferation or survival of a hematopoietic cell using these fragments are also disclosed. In one embodiment, methods are disclosed for stimulating the growth or survival of a hematopoietic stem cell with a fragment of vasostatin, in the presence of a growth factor.

16 Claims, 25 Drawing Sheets

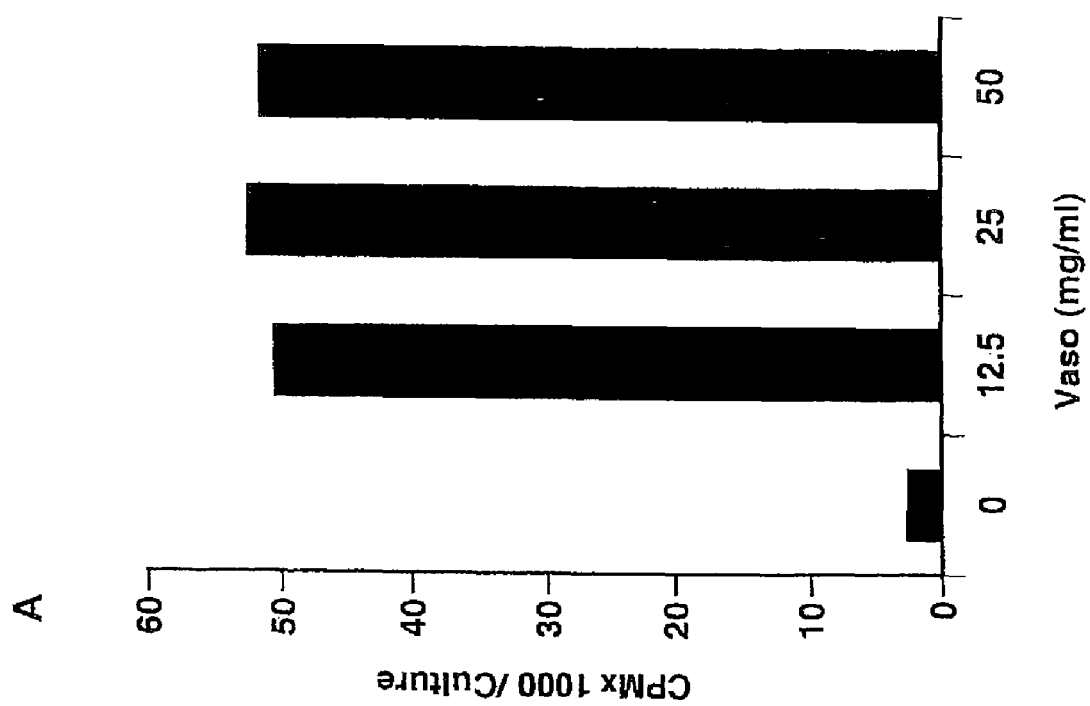

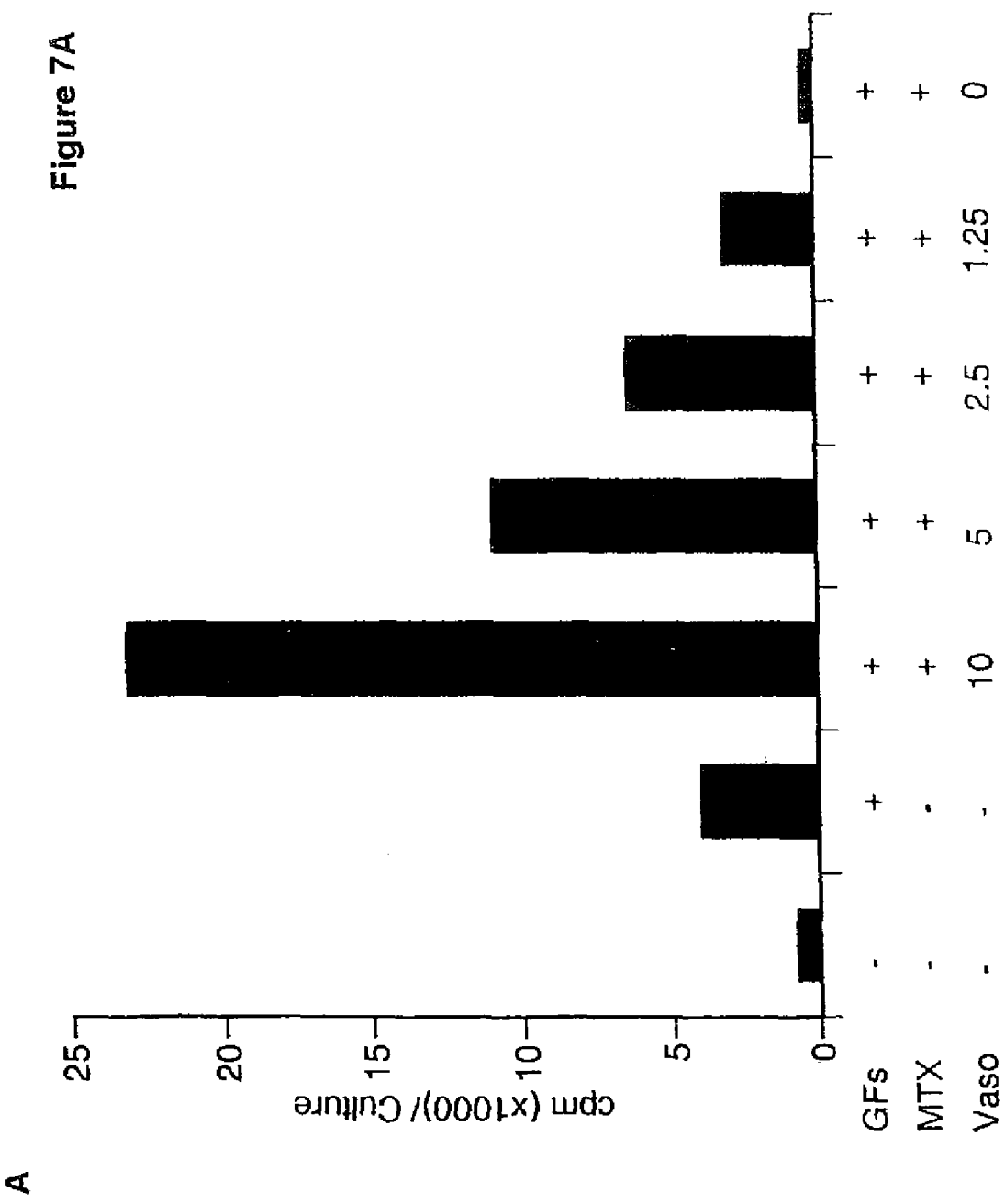

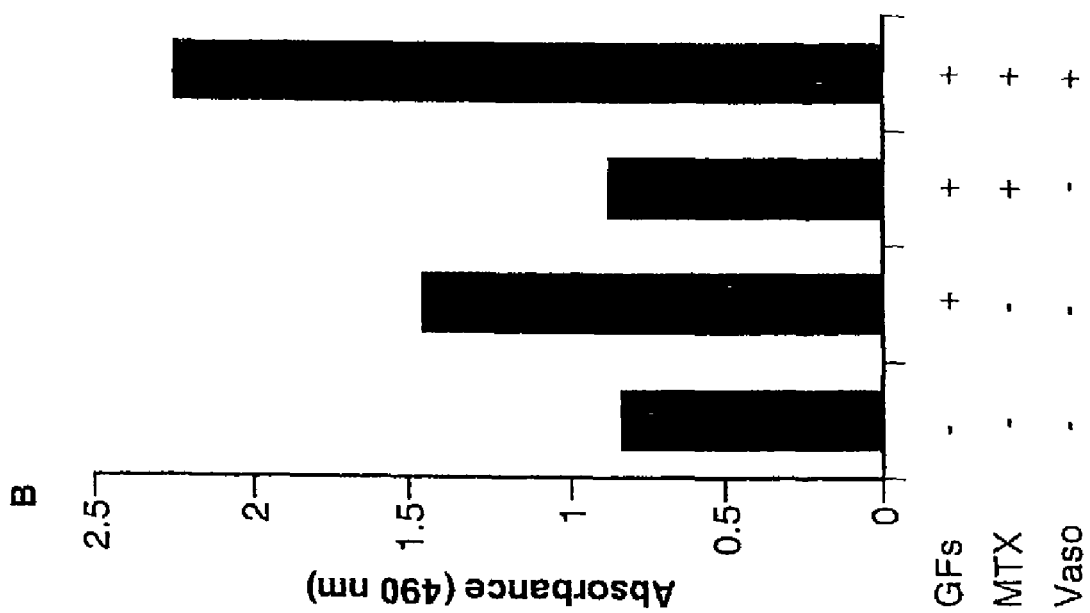

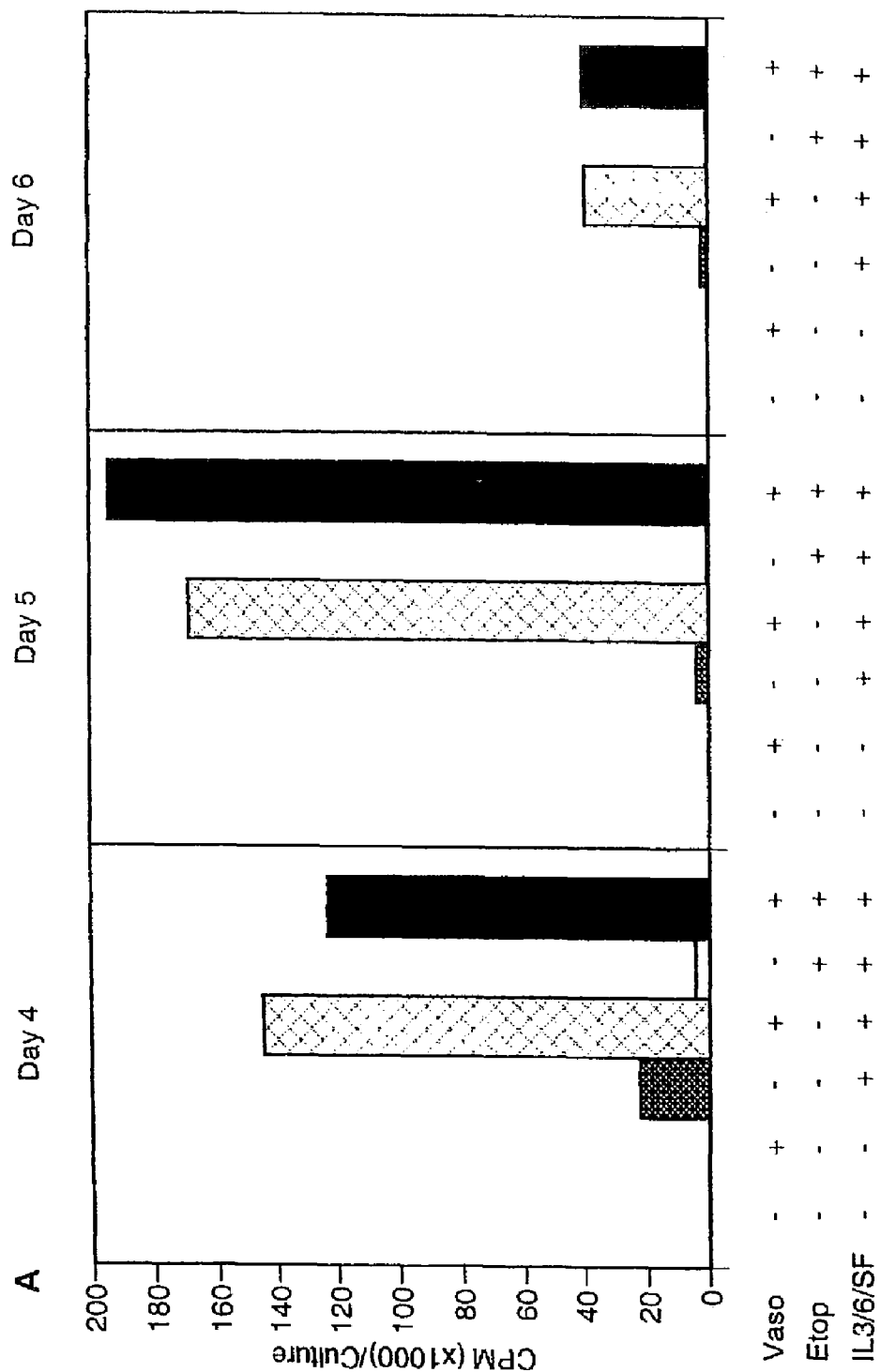

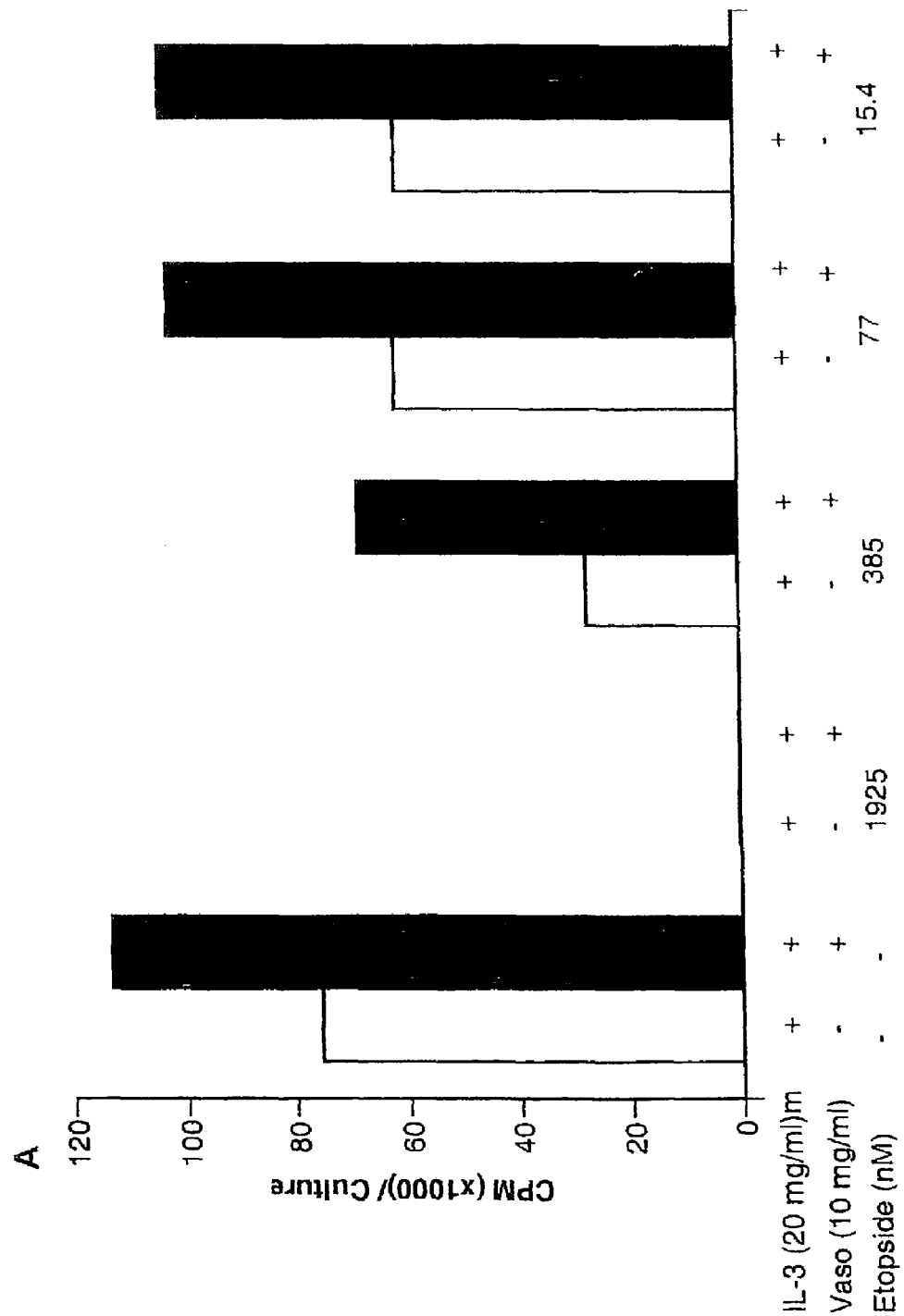

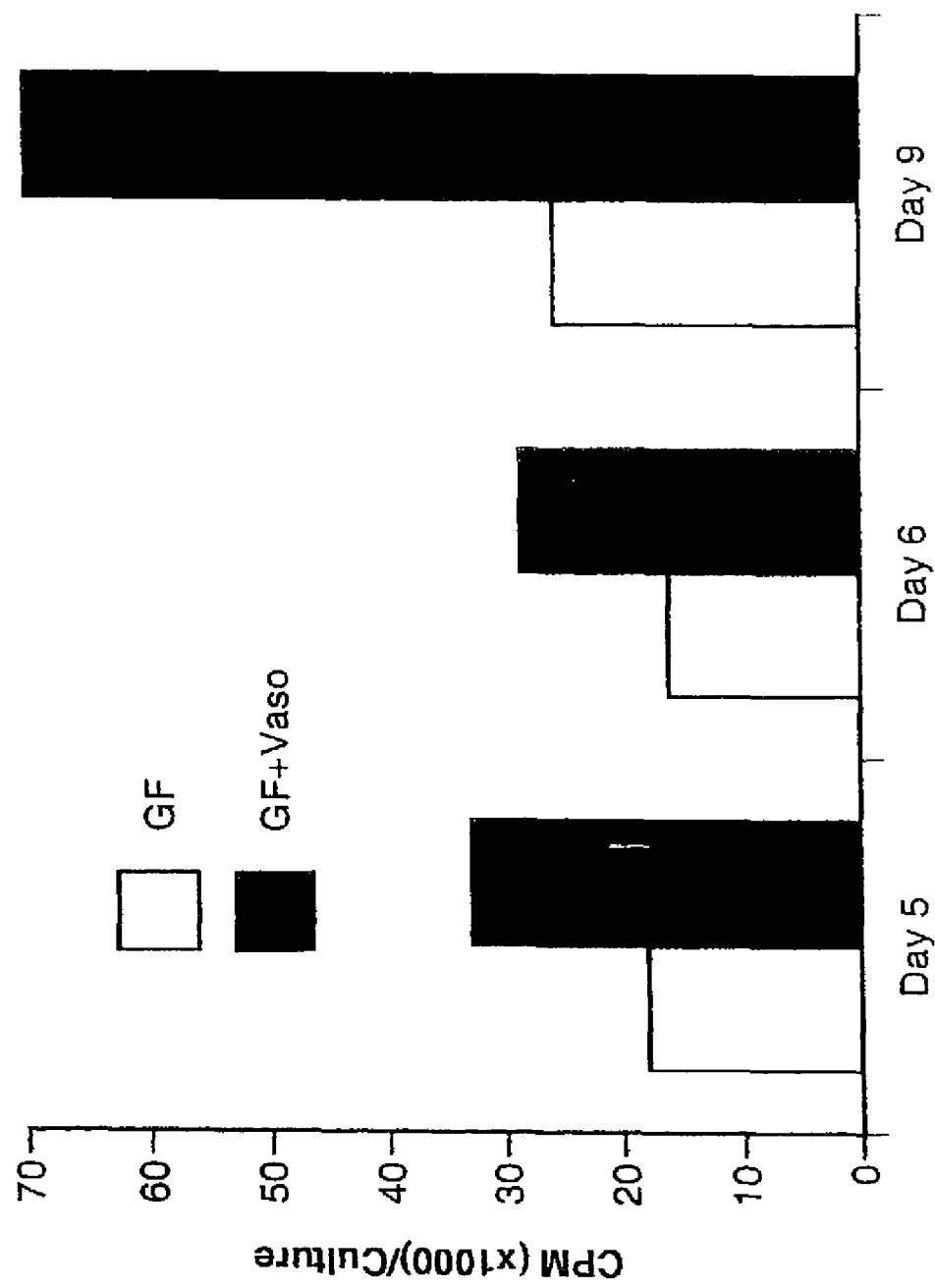

SEQUENCE LISTING

<160> NUMBER OF SEQ ID NOS: 8

<210> SEQ ID NO 1
<211> LENGTH: 1251
<212> TYPE: DNA
<213> ORGANISM: Calreticulin

<400> SEQUENCE: 1

```
atgctgctat ccgtgccgtt gctgctcggc ctcctcggcc tggccgtcgc cgagcctgcc      60
gtctacttca aggagcagtt tctggacgga cacgggtgga cttcccgctg gatcgaatcc     120
aaacacaagt cagattttgg caaattcgtt ctcagttccg gcaagttcta cggtgacgag     180
gagaaagata aggtttgca gacaagccag gatgcacgct tttatgctct gtcggccagt     240
ttcgagcctt tcagcaacaa aggccagacg ctggtggtgc agttcacggt gaaacatgag     300
cagaacatcg actgtggggg cggctatgtg aagctgtttc ctaatagttt ggaccagaca     360
gacatgcacg gagactcaga atacaacatc atgtttggtc ccgacatctg tggccctggc     420
accaagaagg ttcatgtcat cttcaactac aagggcaaga acgtgctgat caacaaggac     480
atccgttgca aggatgatga gtttacacac ctgtacacac tgattgtgcg gccagacaac     540
acctatgagg tgaagattga acacagccag gtggagtccg gctccttgga agacgattgg     600
gacttcctgc cacccaagaa gataaaggat cctgatgctt caaaaccgga agactgggat     660
gagcgggcca agatcgatga tcccacagac tccaagcctg aggactggga caagcccgag     720
catatccctg accctgatgc taagaagccc gaggactggg atgaagagat ggacggagag     780
tgggaacccc cagtgattca gaaccctgag tacaagggtg agtggaagcc ccggcagatc     840
gacaacccag attacaaggg cacttggatc cacccagaaa ttgacaaccc cgagtattct     900
cccgatccca gtatctatgc ctatgataac tttggcgtgc tgggcctgga cctctggcag     960
gtcaagtctg gcaccatctt tgacaacttc ctcatcacca acgatgaggc atacgctgag    1020
gagtttggca acgagacgtg gggcgtaaca aaggcagcag agaaacaaat gaaggacaaa    1080
caggacgagg agcagaggct taaggaggag gaagaagaca gaaacgcaa agaggaggag    1140 gaggcagagg acaaggagga tgatgaggac aaagatgagg atgaggagga tgaggaggac    1200
aaggaggaag atgaggagga agatgtcccc ggccaggcca aggacgagct g             1251
```

<210> SEQ ID NO 2
<211> LENGTH: 416
<212> TYPE: PRT
<213> ORGANISM: Calreticulin

<400> SEQUENCE: 2

```
Met Leu Leu Ser Val Pro Leu Leu Gly Leu Leu Gly Leu Ala Val
1               5                   10                  15

Ala Glu Pro Ala Val Tyr Phe Lys Glu Gln Phe Leu Asp Gly Asp Gly
            20                  25                  30

Trp Thr Ser Arg Trp Ile Glu Ser Lys His Lys Ser Asp Phe Gly Lys
        35                  40                  45

Phe Val Leu Ser Ser Gly Lys Phe Tyr Gly Asp Glu Glu Lys Asp Lys
    50                  55                  60
```

```
Gly Leu Gln Thr Ser Gln Asp Ala Arg Phe Tyr Ala Leu Ser Ala Ser
 65                  70                  75                  80

Phe Glu Pro Phe Ser Asn Lys Gly Gln Thr Leu Val Val Gln Phe Thr
                 85                  90                  95

Val Lys His Glu Gln Asn Ile Asp Cys Gly Gly Tyr Val Lys Leu
            100                 105                 110

Phe Pro Asn Ser Leu Asp Gln Thr Asp Met His Gly Asp Ser Glu Tyr
                115                 120                 125

Asn Ile Met Phe Gly Pro Asp Ile Cys Gly Pro Gly Thr Lys Lys Val
130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
                180                 185                 190

Ser Gly Ser Leu Glu Asp Asp Trp Asp Phe Leu Pro Pro Lys Lys Ile
            195                 200                 205

Lys Asp Pro Asp Ala Ser Lys Pro Glu Asp Trp Asp Glu Arg Ala Lys
210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
                260                 265                 270

Gly Glu Trp Lys Pro Arg Gln Ile Asp Asn Pro Asp Tyr Lys Gly Thr
            275                 280                 285

Trp Ile His Pro Glu Ile Asp Asn Pro Glu Tyr Ser Pro Asp Pro Ser
290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
                340                 345                 350

Ala Glu Lys Gln Met Lys Asp Lys Gln Asp Glu Glu Gln Arg Leu Lys
            355                 360                 365

Glu Glu Glu Glu Asp Lys Lys Arg Lys Glu Glu Glu Glu Ala Glu Asp
            370                 375                 380

Lys Glu Asp Asp Glu Asp Lys Asp Glu Asp Glu Asp Glu Glu Asp
385                 390                 395                 400

Lys Glu Glu Asp Glu Glu Glu Asp Val Pro Gly Gln Ala Lys Asp Glu
                405                 410                 415

<210> SEQ ID NO 3
<211> LENGTH: 180
<212> TYPE: PRT
<213> ORGANISM: Vasostatin

<400> SEQUENCE: 3

Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
            20                  25                  30
```

```
Val Leu Ser Ser Gly Lys Phe Tyr Gly Asp Glu Glu Lys Asp Lys Gly
            35                  40                  45

Leu Gln Thr Ser Gln Asp Ala Arg Phe Tyr Ala Leu Ser Ala Ser Phe
        50                  55                  60

Glu Pro Phe Ser Asn Lys Gly Gln Thr Leu Val Val Gln Phe Thr Val
 65                  70                  75                  80

Lys His Glu Gln Asn Ile Asp Cys Gly Gly Gly Tyr Val Lys Leu Phe
                    85                  90                  95

Pro Asn Ser Leu Asp Gln Thr Asp Met His Gly Asp Ser Glu Tyr Asn
                100                 105                 110

Ile Met Phe Gly Pro Asp Ile Cys Gly Pro Gly Thr Lys Lys Val His
                115                 120                 125

Val Ile Phe Asn Tyr Lys Gly Lys Asn Val Leu Ile Asn Lys Asp Ile
        130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu
            180

<210> SEQ ID NO 4
<211> LENGTH: 61
<212> TYPE: PRT
<213> ORGANISM: Fragment 1

<400> SEQUENCE: 4

Thr Asp Met His Gly Asp Ser Glu Tyr Asn Ile Met Phe Gly Pro Asp
  1               5                  10                  15

Ile Cys Gly Pro Gly Thr Lys Lys Val His Val Ile Phe Asn Tyr Lys
                 20                  25                  30

Gly Lys Asn Val Leu Ile Asn Lys Asp Ile Arg Cys Lys Asp Asp Glu
            35                  40                  45

Phe Thr His Leu Tyr Thr Leu Ile Val Arg Pro Asp Asn
        50                  55                  60

<210> SEQ ID NO 5
<211> LENGTH: 27
<212> TYPE: PRT
<213> ORGANISM: Fragment 2

<400> SEQUENCE: 5

Cys Gly Pro Gly Thr Lys Lys Val His Val Ile Phe Asn Tyr Lys Gly
  1               5                  10                  15

Lys Asn Val Leu Ile Asn Lys Asp Ile Arg Cys
            20                  25

<210> SEQ ID NO 6
<211> LENGTH: 18
<212> TYPE: PRT
<213> ORGANISM: Fragment 3

<400> SEQUENCE: 6

Val Ile Phe Asn Tyr Lys Gly Lys Asn Val Leu Ile Asn Lys Asp Ile
  1               5                  10                  15

Arg Cys
```

```
<210> SEQ ID NO 7
<211> LENGTH: 35
<212> TYPE: PRT
<213> ORGANISM: Fragment 4

<400> SEQUENCE: 7

Val Ile Phe Asn Tyr Lys Gly Lys Asn Val Leu Ile Asn Lys Asp Ile
1               5                   10                  15

Arg Cys Lys Asp Asp Glu Phe Thr His Leu Tyr Thr Leu Ile Val Arg
            20                  25                  30

Pro Asp Asn
        35

<210> SEQ ID NO 8
<211> LENGTH: 61
<212> TYPE: PRT
<213> ORGANISM: Fragment 5

<400> SEQUENCE: 8

Cys Gly Pro Gly Thr Lys Lys Val His Val Ile Phe Asn Tyr Lys Gly
1               5                   10                  15

Lys Asn Val Leu Ile Asn Lys Asp Ile Arg Cys Lys Asp Asp Glu Phe
            20                  25                  30

Thr His Leu Tyr Thr Leu Ile Val Arg Pro Asp Asn Thr Tyr Glu Val
        35                  40                  45

Lys Ile Asp Asn Ser Gln Val Glu Ser Gly Ser Leu Glu
    50                  55                  60
```

VASOSTATIN AS MARROW PROTECTANT

CROSS REFERENCE TO RELATED APPLICATIONS

This is a divisional of U.S. patent application Ser. No. 10/405,588, filed Apr. 1, 2003 now U.S. Pat. No. 7,432,236, which is a divisional of U.S. patent application Ser. No. 09/828,000, filed Apr. 6, 2001 now U.S. Pat. No. 6,596,690, which is a continuation-in-part of International (PCT) Application No. US99/23240, filed Oct. 5, 1999, which claims the benefit of U.S. Provisional Application No. 60/103,438, filed Oct. 6, 1998. The prior applications are all incorporated by reference herein in their entirety.

FIELD OF THE INVENTION

This application relates to stimulation of hematopoiesis, more specifically to the protection of stem cells from toxic agents.

BACKGROUND

A. Hematopoiesis

The mammalian hematopoietic system represents the source for the continuous production of large numbers of mature cell populations, that collectively represent the different array of peripheral blood lineages. Transplantation studies over the last four decades have defined operationally the activities of a rare bone marrow stem cell that is multipotential in its ability to give rise to mature blood cells and has self-renewal potential. Thus, it is currently believed that hematopoiesis is sustained by uncommitted stem cells that generate committed precursors that are capable of producing mature blood cells of all lineages (Dieterlen-Lievre et al., Int Arch Allergy Immunol, 112, 3-8, 1997; Morrison et al., Development, 124:1929-39, 1997).

Hematopoietic stem cells are self-regenerating, and also pluripotent in that they differentiate into several lineages, including lymphoid, myeloid and erythroid lineages. The lymphoid lineage, comprising B-cells and T-cells, provides for the production of antibodies, regulation of the cellular immune system, detection of foreign agents in the blood, detection of cells foreign to the host, and the like. The myeloid lineage, which includes monocytes, granulocytes, megakaryocytes as well as other cells, monitors for the presence of foreign bodies in the blood stream, provides protection against neoplastic cells, scavenges foreign materials in the blood stream, produces platelets, and the like. The erythroid lineage provides the red blood cells, which act as oxygen carriers. Exposure to growth factors is believed to induce a stem cell to be dedicated to differentiate into a specific lineage.

Many strategies have been developed to physically purify hematopoietic stem cells from the bone marrow or other sources such as the peripheral blood or fetal liver (Goodell et al., J Exp Med, 183:1797-806, 1996; Goodell et al., Nat Med, 3:1337-45, 1997; Lemischka et al. Cell, 45:917-27, 1986; Spangrude et al., Science, 241:58-62, 1988; Wolf et al., Exp Hematol, 21:614-22, 1993). However, the identity of the stem cells has remained elusive, and the only reliable measure of stem cell activity in any type of purified stem cell population is by in vivo transplantation. Remarkably, in some cases, it has been possible to demonstrate that a single stem cell is both necessary and sufficient to reconstitute a normal hematopoietic system into a recipient host (Jordan and Lemischka, Genes Dev, 4:220-32 1990; Osawa et al., Science, 273:242-5, 1996).

Recently, several studies have provided evidence for the existence of stem cells in several somatic tissues (Doetsch et al., Cell, 97:703-16, 1999; Gussoni et al., Nature, 401:390-4, 1999; Jackson et al., PNAS USA, 96:14482-6, 1999; Johansson et al., Cell, 96:25-34, 1999; Potten et al., Int J Exp Pathol, 78:219-43, 1997; Reynolds and Weiss, Science, 255:1707-10, 1992). Somatic tissues were previously believed to contain somatic stem cell populations capable of self-renewing potential but with a limited degree of lineage plasticity. However, transplantable hematopoietic cells were recently identified from muscle (Gussoni et al., Nature, 401:390-4, 1999; Jackson et al., PNAS USA, 96:14482-6, 1999).

Hematopoiesis is governed by a complex set of cytokines that variously regulate stem cell functions (Dieterlen-Lievre, Curr Biol, 8:R727-30, 1998; Ogawa, Blood, 81:2844-53, 1993). Individual cytokines and various combinations of these cytokines have been shown to maintain and promote the differentiation of populations of stem cells. In the mouse, cytokines have also been shown to modesty expand stem cells that are capable of long-term hematopoietic reconstitution of recipient animals (Dieterlen-Lievre, Curr Biol, 8:R727-30, 1998; Ogawa, Blood, 81:2844-53, 1993). However, the inability to consistently sustain and expand hematopoietic stem cells in vitro and in vivo represents a major barrier for further understanding the biology of stem cells and the ability to utilize such cells for therapeutic interventions. For example, use of chemotherapeutic agents for cancer therapy is often limited by hematopoietic stem cell toxicity and gene therapy approached to correction of genetic deficiencies is hampered by efficient gene transfer of cells with self-renewing potential (Dick, Nat Med, 6:624-6, 2000; Halene and Kohn, Hum Gene Ther, 11:1259-67, 2000; Mulligan, Science, 260:926-32, 1993). Thus, there is a need for identification of novel agents that promote stem cell survival and proliferation.

B. Calreticulin

Calreticulin was first identified in skeletal muscle sarcoplasmic reticulum. (Ostwald and MacLennan, J. Biol. Chem. 249 (3):974-979, 1974). Fifteen years later it was cloned and the N-terminus was sequenced. This led to the discovery that several groups had independently identified the molecule and had given it different names, including, "high-affinity $Ca^{2+}$", "calregulin", "CRP55" and "calsequestrin-like protein" (Ostwald and MacLennan, J. Biol. Chem. 249 (3):974-979, 1974; Waisman et al., J. Biol. Chem. 260(3):1652-1660, 1985; Macer, D. R. J. & Koch, G. L. E. J. Cell. Sci. 91:61-70, 1988; Damiani et al., Biochem Biophys Res Commun 165(3):973-980, 1989; Treves et al., Biochem. J. 271:473-480, 1990). Each of these groups identified calreticulin through different means, but all identified its ability to bind $Ca^{2+}$.

Although most studies have indicated that calreticulin resides predominantly within the lumen of the endoplasmic reticulum, calreticulin may also be found in other cellular compartments. For example, calreticulin was detected on the plasma membranes of lymphoblastoid cells (Newkirk and Tsoukas, J. Autoimmun. 5:511-525, 1992) and epidermal keratinocyte lines (Kawashima, et al., Dermatology 189 Suppl. 1:6-10, 1994). It was proposed to represent, or to be closely related in structure, to the C1q receptor found on endothelial cells, B cells, T cells and other cells (Chen et al., J. Immunol. 153:1430-1440, 1994). Calreticulin is also a constituent of lytic granules contained in cytotoxic T and NK cells from which it is released during cell lysis (Dupuis et al., J. Exp. Med. 177:1-7, 1993), and has been purified from the culture supernatant of several cell types (Booth and Koch, *Cell* 59:729-737, 1989; Eggleton et al., *Clin. Immunol. Immunopathol.* 72:405-409, 1994) and from normal human plasma (Sueyoshi et al., *Thromb. Res.* 63:569-575, 1991). Several observations support the notion that calreticulin can also be a target for autoimmune responses (Lux et al., *J. Clin. Invest.* 89:1945-1951, 1992; Meilof et al., *J. Immunol.* 151:5800-5809, 1993).

Since the initial identification and cloning, the structure of calreticulin has been characterized. Mammalian calreticulin is a 417 amino acid peptide from which the 17 N-terminal amino acids are cleaved upon translocation to the lumen of the endoplasmic reticulum (Smith and Koch, *Embo. J.* 8(12): 3581-3586, 1989). In addition to being found in the lumen of the endoplasmic reticulum, calreticulin has been found in the cytoplasm, in the nucleus of some cells, and in the extracellular matrix (Michalak et al., *Biochem. J.* 285:681-692, 1992). Further studies revealed that calreticulin has three distinct domains, the N-terminal domain, a middle domain and the C-terminal domain.

The mature calreticulin is composed of an N-terminal domain consisting of 180 amino acids that are highly conserved. Proposed three-dimensional models indicate that the domain contains eight anti-parallel β-strands. Furthermore, the N-terminal domain has been found to bind a number of molecules including the alpha subunit of integrin, $Zn^{2+}$, and the DNA binding domain of steroid receptors (Nash et al., *Mol. Cellular Biochem.* 135:71-78, 1994). The N-terminal domain of calreticulin is also know as vasostatin (vaso) (Pike et al., *J. Exp. Med.,* 188:2349-56, 1998).

The middle domain of calreticulin stretches from amino acid 181 to amino acid 280. It is proline rich and has also been termed the P-domain. This domain has been found to have a high affinity for $Ca^{2+}$ and contains a nuclear localization signal (Baksh and Michalak, *J. Biol. Chem.* 266:21458-21465, 1991).

Following the P-domain is the C-domain that includes the terminal 290-417 amino acids. This last domain is highly acidic and contains an endoplasmic reticulum retention signal. The C-domain binds to Factor IX, Factor X, and prothrombin (See U.S. Pat. No. 5,426,097, to Stern et al.).

Calreticulin has also been found to be useful in wound healing (See U.S. Pat. No. 5,591,716, to Siebert et al.).

SUMMARY

The present application stems from the discovery of three previously uncharacterized properties of calreticulin. First, calreticulin N-domain (vaso) is shown to stimulate the proliferation and survival in vitro of hematopoietic cells in the presence of previously identified growth factors. Second, calreticulin N-domain (vaso) is shown to protect hematopoietic cells in vitro from toxicity induced by a variety of chemotherapeutic agents. Third, calreticulin N-domain is shown to protect a subject from toxicity to the hematopoietic system induced by chemotherapy or irradiation.

Fragments of the calreticulin N-domain and fusion proteins thereof have been identified that have these activities. In one embodiment, the fragment includes at least about 180 consecutive amino acids, from amino acid 1 to amino acid 180 of calreticulin. One specific, non-limiting example of these fragments is a fragment of from about amino acid 103 to about amino acid 163 of calreticulin. In another embodiment, the fragment includes from about amino acid 120 to about amino acid 146 of calreticulin. In a further embodiment, the fragment includes from about amino acid 129 to about amino acid 146 of calreticulin.

BRIEF DESCRIPTION OF THE DRAWINGS

FIG. 1 is a digital image of the morphological appearance of representative femurs from control mice, mice treated with cyclophosphamide alone or cyclophosphamide plus vaso. Hematoxylin and eosin stain of decalcified femurs (1× magnification).

FIG. 2 is set of bar graphs showing of the effects of vaso on cytoxan-induced bone marrow toxicity evaluated by bone marrow cell counting. Bone marrow cells obtained from the femurs of mice treated with cytoxan alone or with vaso were counted.

FIG. 4 is a set of bar graphs showing the effects of vaso on the hematopoietic system in vivo. Groups of C57BL/6 mice (8 weeks of age) were treated as described in FIG. 14.

FIG. 6 is a series of bar graphs showing the effects of vaso on growth-factor induced proliferation of bone marrow cells with or without mafosfamide. Bone marrow cells populations, obtained from the femural cavities of C57BL/6NCR mice (6 months of age), were cultured in 24 well tissue culture plates in culture medium containing a mixture of IL-3 (20 ng/ml), IL-6 (100 ng/ml) and Stem Cell Factor (100 ng/ml).

FIG. 6A is a bar graph showing bone marrow cell proliferation after 5 days culture with growth factors alone (IL-3 plus IL-6 plus Stem Cell Factor (SF) or with growth factors plus vaso at varying concentrations (12.5-50 µg/ml).

FIG. 7 is a series of bar graphs showing the effects of vaso on growth-factor induced proliferation of bone marrow cells with or without methotrexate. Bone marrow cells populations, obtained from the femural cavities of C57BL/6NCR mice (3.5 months of age), were cultured in 24 well tissue culture plates in culture medium alone or medium containing a mixture of the growth factors (GF) IL-3 (20 ng/ml), IL-6 (100 ng/ml) and Stem Cell Factor (100 ng/ml). Vaso was added to the cultures at concentrations ranging between 1.25 and 10 µg/ml. Methotrexate was added to the cultures at the concentration of 100 nM. FIG. 7A is a bar graph of cell proliferation as measured by $^3$H thymidine incorporation during the final 22 hr of a 7-day culture. The results reflect the mean cpm of triplicate cultures. FIG. 7B is a bar graph of cell numbers measured as mean absorbance (490 nM) after conversion of Owen's reagent into colored formazan product (One Solution Reagent, Promega).

FIG. 8 is a series of graphs showing the effects of vaso on the proliferation of murine bone marrow cells. Bone marrow cells populations, obtained from the femural cavities of C57BL/6NCR mice (4 months of age), were cultured in 24 well tissue culture plates in culture medium containing IL-3 alone (20 ng/ml) or a mixture of IL-3 (20 ng/ml), IL-6 (100 ng/ml) and Stem Cell Factor (SF, 100 ng/ml). Vaso (10 µg/ml) was added at the time the cultures were initiated. At the indicated time-points (day 3, day 4, day 5, or day 6), cell proliferation was measured by $^3$H thymidine incorporation over the final 20-23 hr of culture.

FIG. 9A is a bar graph of cell proliferation as measured by $^3$H thymidine incorporation during the final 20-23 hr of a 4, 5 or 6-day culture. FIG. 9B is a bar graph of cell number measured as absorbance (490 nM) after conversion of Owen's reagent into colored formazan product (One Solution Reagent, Promega).

FIG. 10 is a series of bar graphs showing the effects of vaso on bone marrow cell proliferation in vitro. Bone marrow cell populations, obtained from the femural cavities of C57BL/6NCR mice (9 weeks of age), were incubated in culture medium supplemented with IL-3 (20 ng/ml) with or without vaso (10 µg/ml). FIG. 10A is a bar graph of cell proliferation when etoposide was added to the IL-3 supplemented cultures at concentrations ranging between 15.4 and 1924 nM, with or without vaso. Cell proliferation was measured on day 5 of culture by $^3$H thymidine incorporation. Means of triplicate cultures.

FIG. 12 is a bar graph of the proliferative responses of human CD34-positive cells to vaso. Human CD34-positive cells purified (>90% purity) from the peripheral blood of a normal individual after G-CSF mobilization following standard procedures were cultured (1×10$^6$ cells/ml) in 24 well tissue culture plates in RPMI 1640 medium supplemented with 15% FBS. The growth factors (GF) Stem Cell Factor (300 ng/ml) plus Flt-3 ligand (300 ng/ml) were added to the culture medium. Vaso was added at 10 µg/ml. Cell proliferation was measured during the final 22 hr of a 5, 6 or 9 day culture by $^3$H thymidine incorporation. Data is shown as the mean of triplicate cultures.

FIG. 13 is a series of bar graphs showing the effects of calreticulin fragments on the proliferation of murine bone marrow cell populations. Cells obtained from the femural bone marrow of mice (C57BL/6NCR mice, 6 weeks of age) were cultured in medium containing IL-3 (20 ng/ml) with or without the addition of recombinant vaso (10 µg/ml) or calreticulin fragments. Proliferation was measured by $^3$H thymidine incorporation on day 5 or 6 of culture. The results reflect the mean cpm of triplicate cultures (SDs within 10% of the mean).

DETAILED DESCRIPTION OF THE SPECIFIC EMBODIMENTS

Sequences

Figure 1A:
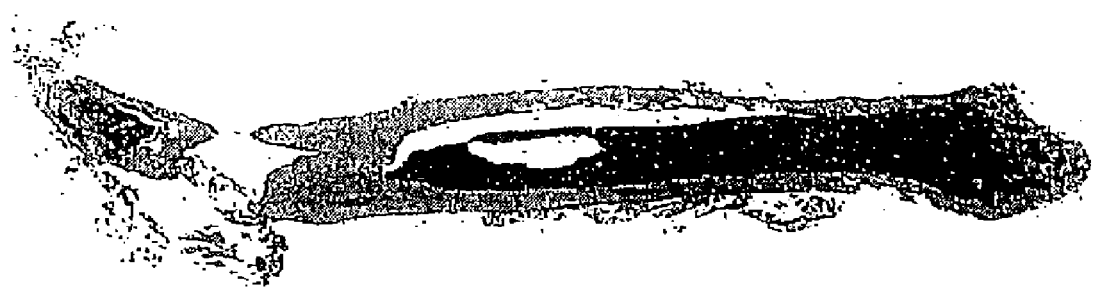
FIG. 1A is a digital image of a femur from a control mouse treated with buffer alone for 26 days, removed on day 27.

SEQ ID NO: 1 is the nucleic acid sequence of calreticulin.
SEQ ID NO:2 is the amino acid sequence of calreticulin.
Mammalian calreticulin is a 417 amino acid peptide from which the seventeen N-terminal amino acids are cleaved upon translocation to the lumen of the endoplasmic reticulum (Smith and Koch, *Embo. J.* 8(12):3581-3586, 1989). Thus, calreticulin is commonly numbered starting from amino acid-17, which is a methoinine (met). Amino acid number 1 is a glutamine (glu).

SEQ ID NO:3 is the amino acid sequence of a fragment of calreticulin from amino acid 1 to amino acid 180, also known as vasostatin.

SEQ ID NO:4 is the amino acid sequence of a fragment of vasostatin from amino acid 103 to amino acid 163.

SEQ ID NO:5 is the amino acid sequence of a fragment of calreticulin from amino acid 120 to amino acid 146.

SEQ ID NO:6 is the amino acid sequence of a fragment of calreticulin from amino acid 129 to amino acid 146.

SEQ ID NO:7 is the amino acid sequence of a fragment of calreticulin from amino acid 129 to amino acid 163.

SEQ ID NO:8 is the amino acid sequence of a fragment of calreticulin from amino acid 120 to amino acid 180.

The sequences of calreticulin and vasostatin are shown in US99/23240, filed Oct. 5, 1999, which is a continuation of U.S. Provisional Application No. 60/103,438, Oct. 6, 1998, both of which are incoporated by reference herein in their entirity.

DEFINITIONS

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). 5,753,500.

Agent that affects hematopoiesis: A compound, antibody, nucleic acid molecule or protein that affects hematopoiesis. In one embodiment, the agent affects the growth, proliferation, maturation, or differentiation of hematopoietic cells. An agent can be a naturally occurring molecule or a synthetic molecule, such as a fragment of calreticulin.

Calreticulin: Calreticulin is a calcium binding protein that is found in many animals, and is highly conserved across species. The open reading frame of the prototypical human calreticulin is shown in SEQ ID NO: 1, while the sequence of the human calreticulin protein is shown in SEQ ID NO: 2. The present application is founded on the discovery that calreticulin, and fragments of the C protein of calreticulin, possess certain biological activities ("calreticulin activities"). Specifically, these activities include protection of bone marrow cells, such as hematopoietic stem cells, from chemotherapy or irradiation.

Each of these activities may be separately assayed by methods described herein. The ability of calreticulin or a fragment of this protein to perform these activities may be beneficial in a number of applications, including clinical applications such as tumor therapy, wherein protection of the stem cells is desired.

While the amino acid sequence of the prototypical human calreticulin is shown in SEQ ID NO:2, one of skill in the art will appreciate that variations in this amino acid sequence (such as amino acid deletions, additions or substitutions) may be made without substantially affecting the activities of the protein (or fragments of the protein) discussed above. Thus, reference herein to the term "calreticulin" encompasses both the protein having the amino acid sequence shown in SEQ ID NO:2, as well as amino acid sequences that are based on this sequence but which include one or more sequence variants. Such sequence variants may also be defined in the degree of amino acid sequence identity that they share with the amino acid sequence shown in SEQ ID NO: 2, or in the degree of amino acid sequence identity that they show with a fragment of calreticulin, such as the N-terminal domain of calreticulin. One specific, non-limiting example of a fragment of calreticulin or a variant thereof is the N-terminal domain of calreticulin, of from amino acid 1 to amino acid 180 of calreticulin (SEQ IN NO: 3, hereinafter vasostatin, or "vaso"). In one embodiment, a fragment is at least about 18 consecutive amino acids of vasostatin, or at least about 25 amino acids of vasostatin, or at least about 30 amino acids of vasostatin. Specific, non-limiting examples of a fragment of vasostatin are a fragment from about amino acid 103 to about 163 of vaso (SEQ ID NO:4), or a fragment from about 120 to about amino acid 146 of vaso (SEQ ID NO:5), or a fragment of from about amino acid 128 to about amino acid 146 of vaso, (SEQ ID NO:6), or a fragment of from about amino acid 129 to about amino acid 163 (SEQ ID NO: 7) of vaso. Additional fragments include, but are not limited to, a fragment of vasostatin from about amino acid 120 to about amino acid 150, a fragment of vasostatin from about amino acid 100 to about amino acid 160, a fragment of vasostatin from about amino acid 110 to about amino acid 150, a fragment of vasostatin from about amino acid 120 to about amino acid 150. In one embodiment, a fragment of vasostatin is any fragment of vasostatin that includes the twenty-seven consecutive amino acids from amino acid 120 to amino acid 146 of vasostatin. One of skill in the art, given the disclosure and assays described herein, can readily identify other fragments of vasostatin, or a variant thereof, that affect hematopoiesis or that protect hematopoeitic cells from the toxicity associated with chemotherapy or irradiation.

Typically, a variant of vasostatin will share at least 80% sequence identity with a related sequence. More highly conserved variants will share at least 90% or at least 95% sequence identity with the related sequence. In addition to sharing sequence identity with the prototypical vasostatin protein sequence, or a fragment thereof such sequence, variants also affect hematopoiesis or protect hematopoietic cells from the toxicity associated with chemotherapy or irradiation.

Carrier protein: A protein or a polypeptide that can be fused to vasostatin, or a fragment thereof, to form a fusion protein. The fusion of vasostatin, or a fragment thereof, to a carrier protein aids in the manipulation of the peptide. In one embodiment, the carrier protein is attached to vasostatin, or the fragment thereof by a linker. Specific, non-limiting examples of a carrier protein are maltose binding protein (MBP), glutathione-S-transferase, or six histine residues (6xhis).

Conservative variants: As demonstrated herein, calreticulin stimulates hematopoiesis and protects hematopoietic cells from the effect of chemotherapy or irradiation). These activities are also found in several peptide fragments of calreticulin. For example, vasostatin (SEQ ID NO:3) possesses these activities. Specific, non-limiting examples of a fragment of use are SEQ ID NO:4, SEQ ID NO:5, and SEQ ID NO:6, or a conservative variant thereof. "Conservative" amino acid substitutions include the following examples:

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Non-conservative substitutions are those that reduce the ability of vasostatin, or a fragment thereof, to promote survival or proliferation of a hemotopoietic cell or to protect from the effect of chemotherapy or irradiation. Thus, conservative substitutions are those substitutions that do not affect or increase the ability of vasostatin, or a fragment thereof, to promote survival of hematopoietic cells or to protect hemotopoietic cells from an effect of chemotherapy or irradiation.

Chemotherapy: The use of agents to treat a neoplastic disease, such as a tumor. Chemotherapeutic agents act by a variety of mechanisms, including cross-linking DNA, inhibition of dihydrofolic acid reductase, inhibition of cell cycle progression, or by cell-cycle non-specific interstrand DNA cross-linking. Specific, non-limiting examples of chemotherapeutic agents are methotrexate, cyclophosphamide, monoclonal antibodies, platinum, etoposide, adriamycin, doxorubicin, biCNU, hydroxiurea, taxol, steroids, fluorouracil, viucristine, interferon-alpha, bleomycin, fludarabin, cytokines, and chemokines.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Differentiation: The process by which cells become more specialized to perform biological functions. Differentiation is a property that is often totally or partially lost by cells that have undergone malignant transformation.

Enhancement (enhancing): An increase in a particular parameter of a cell or organism. In one embodiment, enhancement refers to a 25%, 50%, 100% or greater than 100% increase in a parameter. In one specific, non-limiting example, enhancement of hematopoiesis refers to an increase in a population of the cells of a hematopoietic lineage (e.g. B cells, T cells, macrophages, monocytes, or a hematopoietic intermediate cell), such as a 25%, 50%, or 100% increase in the population of cells or the response of the population of cells.

Growth Factor: A "growth factor" is a substance that affects the growth of a cell or organism. In general, growth factors stimulate cell proliferation, survival, or maturation when they bind to their receptor ("growth factor receptor"). In one embodiment, growth factors are a complex family of polypeptide hormones or biological factors that are control growth, division and maturation of hematopoietic cells. In another embodiment, growth factors regulate the division and proliferation of cells and influence the growth rate of neoplastic tissue (e.g. cancers). A growth factor can be a naturally occurring factor or a factor synthesized using molecular biology techniques. In one specific, non-limiting example, a growth factor can be used to stimulate hematopoiesis, and thus can be used following chemotherapy, irradiation therapy, or bone marrow transplantation.

A growth factor that affects the development (maturation), differentiation, division, or proliferation of hematopoietic cells is a "hematopoietic growth factor." A "stem cell growth factor" is a growth factor that affects hematopoietic stem cells.

Hematopoiesis: The formation and development of blood cells. Hematopoiesis involves the proliferation and differentiation from stem cells. In adult mammals hematopoiesis is known to occur in bone marrow. Hematopoiesis is the production of hematopoietic cells including B Cells, T cells, cells of the monocyte macrophage lineage, and red blood cells.

Inhibition (inhibiting): A decrease in a particular parameter of a cell or organism. In one embodiment, inhibition refers to a 25%, 50%, 100% or greater than 100% decrease in a parameter. In one specific, non-limiting example, inhibition of hematopoiesis refers to a decrease in a population of the cells of a hematopoietic lineage (e.g. B cells, T cells, macrophages, monocytes, or a hematopoietic intermediate cell), such as a 25%, 50%, or 100% decrease in the population of cells or the response of the population of cells.

Irradiation therapy: Treatment by ionizing radiation (radiation sufficient to dislodge electrons from an atom), such as X-rays, alpha particles, or gamma-rays or radioactive sources such as radioactive iodine seeds.

Isolated: An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

$Lin^-$ cell: A hematopoietic stem cell or progenitor cell that does not express a lineage specific (lin) marker. In one embodiment, lineage-committed cells can be identified by incubating the cells with a cocktail of monoclonal antibodies directed at antigens expressed by committed hematopoietic cells; the resulting population of separated cells, which do not express the lineage specific markers, are $Lin^-$ cells. Specific, non-limiting examples of lineage specific markers are CD5, CD45R (B220), CD11b (Mac-1), Myeloid Differentiation Antigen (Gr-1) and Erythroid cells (TER119).

Lymphocytes: A type of white blood cell that is involved in the immune defenses of the body. There are two main types of lymphocytes: B-cell and T-cells.

Lymphoproliferation: An increase in the production of lymphocytes.

Mammal: This term includes both human and non-human mammals. Similarly, the term "subject" includes both human and veterinary subjects.

Mimetic: A molecule (such as an organic chemical compound) that mimics the activity of a protein, such as calreticulin and therapeutically effective variants and fragments thereof. Peptidomimetic and organomimetic embodiments are within the scope of this term, whereby the three-dimensional arrangement of the chemical constituents of such peptido- and organomimetics mimic the three-dimensional arrangement of the peptide backbone and component amino acid sidechains in the peptide, resulting in such peptido- and organomimetics of the peptides having substantial specific inhibitory activity. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press: Buffalo Grove, Ill., pp. 165-174 and *Principles of Pharmacology* (ed. Munson, 1995), chapter 102 for a description of techniques used in computer assisted drug design.

Monocyte: A large white blood cell in the blood that ingests microbes or other cells and foreign particles. When a monocyte passes out of the bloodstream and enters tissues, it develops into a macrophage.

Oligonucleotide: A linear polynucleotide sequence of up to about 100 nucleotide bases in length.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

ORF (open reading frame): A series of nucleotide triplets (codons) coding for amino acids without any termination codons. These sequences are usually translatable into a peptide.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Progenitor Cell: A "progenitor cell" is a cell that gives rise to progeny in a defined cell lineage. A "hematopoietic progenitor cell" is a cell that gives rise to cells of the hematopoietic lineage. One specific non-limiting example of a hematopoietic progenitor cell is a "common lymphoid progenitor cell," which is a progenitor cell that gives rise to immature and mature lymphoid cells. Another specific, non-limiting example of a hematopoietic progenitor cells is a "T cell progenitor cell," which gives rise to immature and mature T cells. Yet another specific, non-limiting example of a progenitor cell is a "stromal progenitor cell," which is a progenitor cell that gives rise to stromal elements.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of calreticulin will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; and Pearson and Lipman, *Proc. Natl. Acad. Sci. U.S.A.* 85:2444, 1988. Altschul et al., *Nature Genet.*, 6:119-129, 1994 presents a detailed consideration of sequence alignment methods and homology calculations.

The NCBI Basic Local Alignment Search Tool (BLAST) (Altschul et al., *J. Mol. Biol.*, 215:403-410, 1990.) is available from several sources, including the National Center for Biotechnology Information (NCBI, Bethesda, Md.) and on the Internet, for use in connection with the sequence analysis programs blastp, blastn, blastx, tblastn and tblastx. A description of how to determine sequence identity using this program is available on the at the NCBI website on the internet.

Homologs and variants of calreticulin or fragments of calreticulin are typically characterized by possession of at least 50% sequence identity counted over the full length alignment with the amino acid sequence of calreticulin using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 60%, at least 65%, at least 70%, at least 75%, at least 80%, at least 90% or at least 95% sequence identity. When less than the entire sequence is being compared for sequence identity, homologs and variants will typically possess at least 75% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Stem Cell: A "stem cell" is a pluripotent cell that gives rise to progeny in all defined hematolymphoid lineages. In addition, limiting numbers of cells are capable of fully reconstituting a seriously immunocompromised subject in all blood cell types and their progenitors, including the pluripotent hematopoietic stem cell, by cell renewal.

Subject: Living multi-cellular vertebrate organisms, a category that includes both human veterinary subjects, including human and non-human mammals.

T Cell: A white blood cell critical to the immune response. T cells include, but are not limited to, CD4+ T cells and CD8+ T cells. A CD4+ T lymphocyte is an immune cell that carries a marker on its surface known as "cluster of differentiation 4" (CD4). These cells, also known as helper T cells, help orchestrate the immune response, including antibody responses as well as killer T cell responses. CD8+ T cells carry the "cluster of differentiation 8" (CD8) marker. In one embodiment, a CD8 T cells is a cytotoxic T lymphocytes. In another embodiment, a CD8 cell is a suppressor T cell.

Therapeutically effective fragments and variants of calreticulin: It is shown herein that not only does calreticulin possess the specified biological activities (protection from toxicity caused by chemotherapy or irradiation), but that such activities are also found in certain peptide fragments of calreticulin. For example, it is shown that the 180 amino acid N-terminal domain of calreticulin (SEQ ID NO: 3), vasostatin, possesses these activities, as do fragments of at least eighteen consecutive amino acids of vasostatin. One specific, non-limiting example of a therapeutically effective fragment of vasostatin is a 27 amino acid fragment (amino acids 120-146 of calreticulin) an 18 amino acid fragment (amino acids 129-146 of calreticulin), and 61 (amino acids 103-163 of calreticulin) amino acid fragments.

Hence, the terms "therapeutically effective fragment of calreticulin" or "therapeutically effective variant of calreticulin" includes any fragment of vasostatin, or variant thereof that protects a hematopoietic cell from the toxicity of a chemotherapeutic agent or radiation, or stimulates hematopoiesis. Whether a given vasostatin fragment or variant possesses one or more of these biological activities can be readily determined by the assays described herein. For example, the ability to stimulate hematopoiesis can readily be determined for any given fragment of calreticulin using the simple in vitro assay described below.

In one embodiment, a therapeutically effective amount of a fragment of vasostatin is used to stimulate hematopoiesis in a subject with a disorder that impairs hematopoiesis. Specific, non-limiting examples of a disorder that impairs hematopoiesis are aplastic anemia, agranulocytosis, and myelodysplastic syndromes.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vasostatin or vaso: The N-terminal domain of calreticulin (amino acids 1-180 of calreticulin, SEQ ID NO:3).

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Methods of Enhancing Hematopoiesis

Previous studies have identified calreticulin, the N-terminal domain of calreticulin (calreticulin amino acids 1-180, also termed vasostatin or vaso) and some fragments of this N-domain as inhibitors of endothelial cell growth in vitro, angiogenesis in vivo and tumor growth in experimental tumor models (See PCT Application No. US99/23240, herein incorporated by reference in its entirety; Pike et al., 1998; Pike et al., 1999; Yao, 2000). These fragments of the N-domain of calreticulin include calreticulin encompassing amino acids 120-180 (Pike et al., 1998; Pike et al., 1999; Yao, 2000). Disclosed herein are fragments of vaso that function for enhancing hematopoiesis or for inhibiting the toxic effects of chemotherapy or irradiation on hematopoietic cells either in vivo or in vitro. In one embodiment, the chemotherapeutic agent is an agent that cross-links DNA, an antimetabolite that inhibits dihydrofolic acid reductase, an inhibitor of cell cycle progression, or a cell-cycle non-specific interstrand DNA crosslinker, such as mafosfamide, etoposide, cisplatinin, or methotrexate.

A method for stimulating the growth of a hematopoietic stem cell is also disclosed herein. The method includes contacting the hematopoietic cell with a peptide comprising at least 18 consecutive amino acids of SEQ ID NO:4 and a growth factor, thereby stimulating the proliferation of the hematopoietic cell. A method is provided for protecting a bone marrow cell in a subject treated with a chemotherapeutic agent or radiation from toxicity caused by chemotherapy or irradiation. The method includes administering to the subject a therapeutically effective amount of vasostatin or a therapeutically effective fragment thereof (e.g. a peptide comprising at least 18 consecutive amino acids of SEQ ID NO:3), thereby protecting the bone marrow cell from the toxicity caused by chemotherapy or irradiation.

Several active fragments of calreticulin are disclosed including vasostatin (amino acids 1-180 of calreticulin), calreticulin encompassing amino acids 103-163 (SE ID NO:4), calreticulin encompassing amino acids 120-146 (SEQ ID NO:5), and calreticulin encompassing amino acids 129-146 (SEQ ID NO:6), and conservative variants thereof. Nucleic acids encoding vasostatin or a therapeutically effective fragment thereof are disclosed, as well as vectors including these nucleic acids, and host cells transformed with these nucleic acids.

EXAMPLES

Example 1

Vasostatin (Vaso) Protects Mice from Toxicity Following Chemotherapy

With the goal of mimicking standard regimens for the treatment of hematological malignancies, a variety of experiments were performed in mice in which chemotherapy or radiation were combined with anti-angiogenic therapy. To this end, mice were inoculated subcutaneously (s.c.) with a human tumor cell line (Burkitt cell line CA46) and treated the animals either with vaso alone or with vaso together with the chemotherapeutic agent cyclophosphamide which is commonly used for the treatment of Burkitt lymphoma in humans. Unexpectedly, mice treated with cyclophosphamide alone were smaller in size and generally appeared less healthy than the mice treated with cyclophosphamide in conjunction with vaso. When these striking results were investigated further, a previously unrecognized property of vaso and its active fragments was discovered, namely that vaso is a stimulant of hematopoiesis and a protector of stem cell toxicity.

Groups of 6-8 athymic BALB/c nu/nu mice, 6 weeks of age, were first irradiated with 400 rad, and 24 hr later were inoculated s.c. with $8 \times 10^6$ Burkitt lymphoma cells (CA46 cell line). Beginning 24 hr after cell inoculation, one group (n=6) of mice received daily s.c. inoculations of buffer alone (100 µl); a second group (n=6) received daily s.c. inoculations of a fusion protein of maltose binding protein and vasostatin, MBP-vaso, alone (200 µg in 100 µl of buffer); a third group (n=8) received daily s.c. inoculations of buffer alone (100 µl) plus cyclophosphamide once on day 9 post cell inoculation (2.6 mg i.p. in 100 µl of buffer); a fourth group (n=8) received daily s.c. inoculations of vaso (200 µg in 100 µl of buffer) plus cyclophosphamide once on day 9 post cell inoculation (2.6 mg i.p. in 100 µl of buffer); a fifth group received daily s.c. inoculations of buffer alone (100 µl) plus daily i.p. inoculations of cyclophosphamide (260 µg/mouse in 100 µl of buffer); and a sixth group received daily s.c. inoculations of vaso (200 µg/mouse in 100 µl of buffer) plus daily i.p. inoculations of cyclophosphamide (260 µg/mouse in 100 µl of buffer).

In the group inoculated once with 2.6 mg cyclophosphamide alone, 7 out of 8 mice in were dead on day 13, and the remaining mouse was dead on day 14. By contrast, 8 of 8 mice that had received daily inoculations of vaso in addition to one dose of 2.6 mg cyclophosphamide were alive and well on day 26. Thus, 0/8 mice that had received high-dose cyclophosphamide were alive on day 26, whereas 8/8 mice that had received high-dose cyclophosphamide plus vasostatin were alive and well on day 26 (p<0.0001). On day 26, the experiment was terminated. No abnormalities were noted on gross and microscopic examination of liver, spleen, kidneys, heart, lung, lymph nodes and bone marrow of the mice that had received high dose cyclophosphamide plus vaso and had survived. Since the dose of cyclophosphamide used is known to cause severe toxicity in mice, it is believed that vaso protected the mice from chemotherapy-induced death.

In contrast to the mice that had received high-dose (2.6 mg/mouse once) cyclophosphamide, all mice treated with low dose (260 µg/mouse for 26 days) daily inoculations of cyclophosphamide alone (8/8) or in conjunction with vasostatin (8/8) were alive on day 28, at which time the experiment was terminated and the effects of therapy examined. The control mice treated with either buffer alone (6/6) or vasostatin alone (6/6) were also alive and well. As expected from its previously described anti-angiogenic and anti-tumor effects, vaso reduced the size (4.85 vs 5.85) and the weight (3.79 vs 6.75 g) of tumors compared to the control tumor-bearing mice injected with buffer alone. The average tumor size was reduced by vaso treatment from 5.85 to 4.85 cm$^2$ and the average weight was reduced from 6.75 g to 3.79 g. Cyclophosphamide (260 µg/mouse for 26 days) alone also reduced the rate of tumor size (from 5.85 to 4.98 cm$^2$) and the weight (from 6.75 to 4.69 g) of tumors compared to the control tumor-bearing mice injected with buffer alone. Thus, individually, vaso and cyclophosphamide similarly reduced tumor size and weight. When vaso and cyclophosphamide were given together, tumor size and weight were further reduced to 3.83 cm$^2$ and 3.31 g.

Figure 1B:
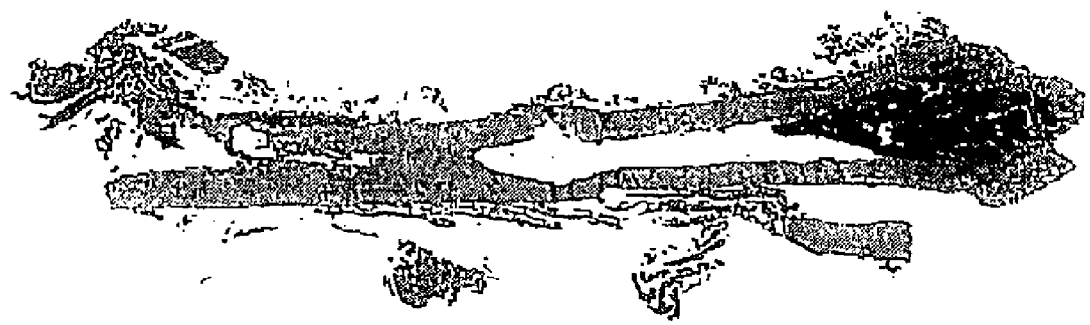
FIG. 1B is a digital image of a femur from a mouse treated with cyclophosphamide (260 µg/day) for 26 days, removed on day 27.
Figure 1C:
FIG. 1C is a digital image of a femur Femur from a mouse treated with cyclophosphamide (260 µg/day) plus vaso (200 µg/day) for 26 days, removed on day 27.

The histological appearance of the bone marrow in mice treated with cyclophosphamide alone was notably different from that of mice treated with cyclophosphamide plus vasostatin or the control mice treated with buffer alone or vasostatin alone (macroscopic morphology shown in FIG. 1). The femoral marrow from cyclophosphamide only treated mice (FIG. 1B) was hypocellular and virtually depleted of hematopoietic cells, with only occasional islands of mature lymphocytes. However, the femoral marrow from animals treated with cyclophosphamide plus vasostatin (FIG. 1C) was indistinguishable from a normal control marrow (FIG. 1A) and displayed normal to increased cellularity, and a normal distribution of hematopoietic cells of all lineages with normal representation of all stages of lineage differentiation. These experiments provided evidence that vaso can protect mice from cyclophosphamide-induced bone marrow toxicity and secondary lethality.

It is known that survival of mice treated with lethal doses of cyclophosphamide can be achieved by injection with bone marrow from normal mice. We found that vaso protected the hematopoietic compartment from drug toxicity. Thus, these data further demonstrated that protection from cyclophosphamide-induced death by vaso is mediated, at least in part, through its activities on the hematopoietic compartment. In addition, these results provide evidence that vaso, while protecting mice from the toxic effects of cyclophosphamide, does not interfere with, but rather contributes to, the anti-tumor efficacy of cyclophosphamide.

Example 2

Figure 2A:
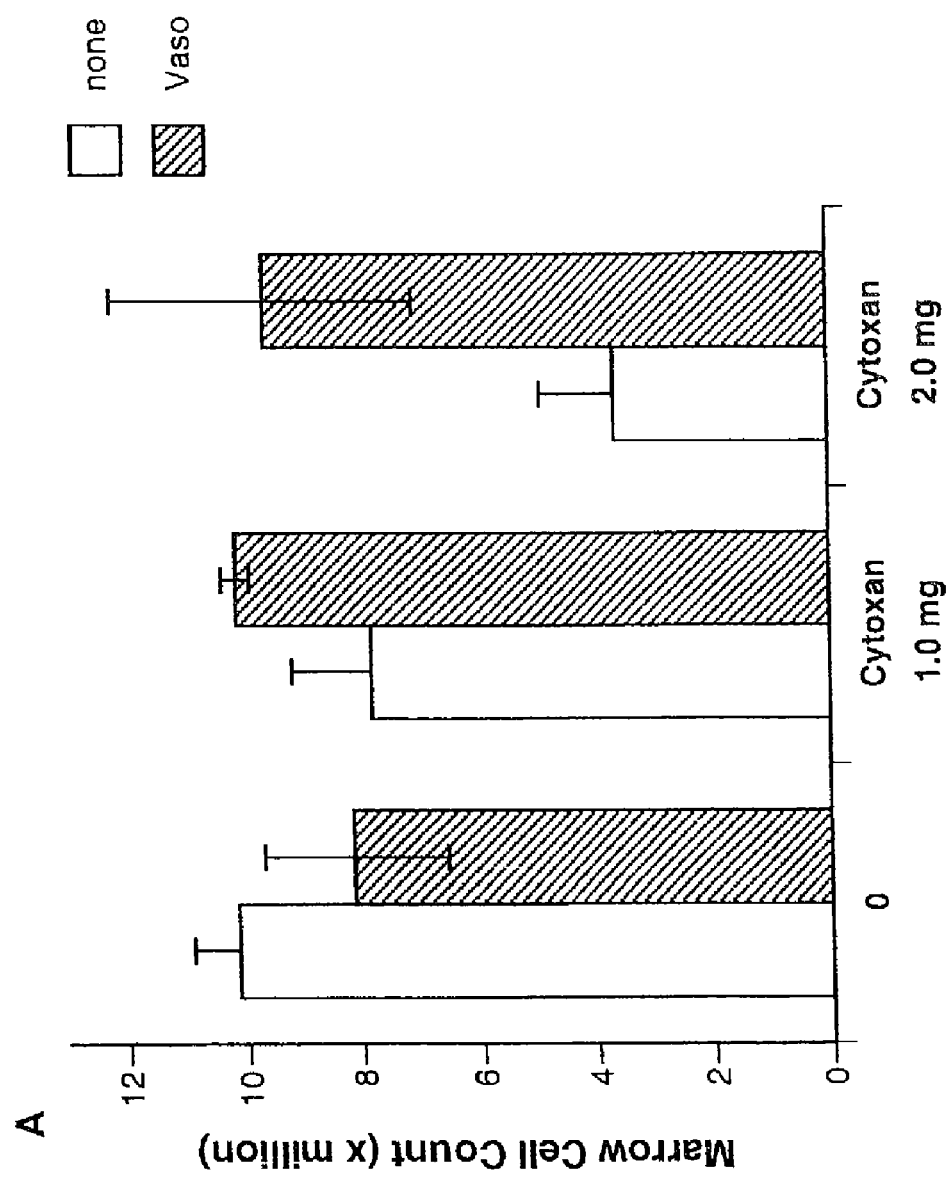
FIG. 2A is a bar graph of bone marrow cell counts 5 days after the injection of cytoxan (1 or 2 mg/mouse) alone or with vaso (300 µg/mouse/day).
Figure 2B:
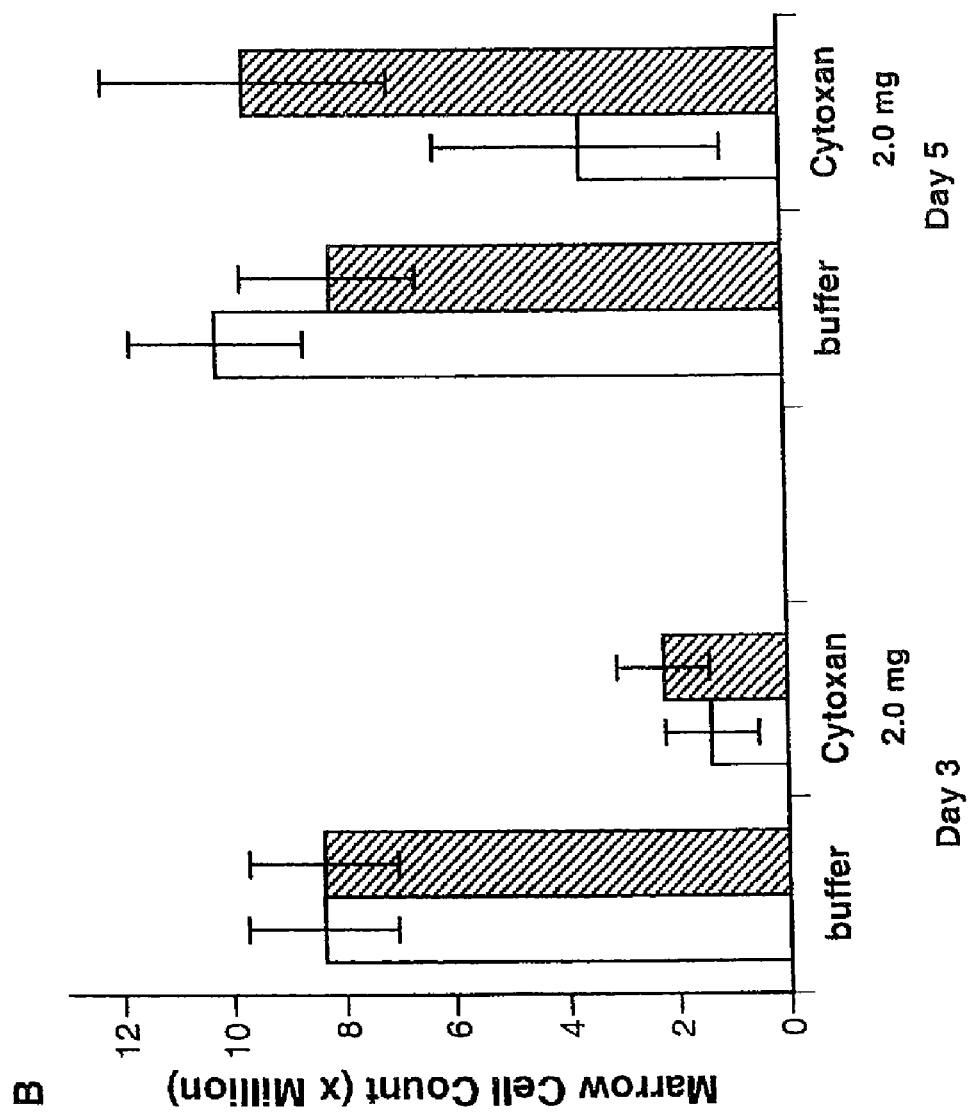
FIG. 2B is a bar graph of the bone marrow cell counts on days 3 and 5 after treatment with cytoxan (2 mg/mouse) alone or with vaso (300 µg/ml).

In Vivo Protection of Hematopoietic Stem Cells from Chemotherapy-Induced Toxicity To more directly test the effects of vaso on hematopoiesis in vivo, an experimental system was used in which cyclophosphamide is administered to mice as a single dose at non-lethal concentrations known to transiently and reproducibly be toxic to the hematopoietic system (DeWys et al., 1970). C57BL6J mice (7 weeks of age) were first treated for 7 days daily with either buffer (100 µl s.c.) or vaso (300 µg/mouse in 100 µl of buffer s.c.). On day 8, groups of mice (n=6) pretreated with either buffer or vaso were injected with cyclophosphamide (1.0 or 2.0 mg/mouse) and continued on daily inoculations of buffer (100 µl s.c.) or vaso (300 µg/mouse in 100 µl of buffer s.c.). Additional control mice were treated with only buffer or vaso for 5 additional days. On days 3 and 5 after cyclophosphamide injection, ½ of the mice were killed for evaluation of the bone marrow and peripheral blood. Bone marrow cell counts in the control mice treated with buffer alone or vaso alone for 12 days were similar, ranging between $8.1 \times 10^6 \pm 1.57$ and $10.1 \times 10^6 \pm 0.76$ cells, indicating that vaso did not significantly alter bone marrow cellularity under the conditions used. As expected, cyclophosphamide given at 1.0 or 2.0 mg/mouse reduced significantly marrow cell counts 5 days later (FIG. 2A). However, when cyclophosphamide was given together with vaso, the reduction in bone marrow cell counts was minimal (FIG. 2A). Maximal reduction of bone marrow cell counts by cyclophosphamide (2 mg/mouse) was noted on day 3 after the drug was injected. Vaso reduced the severity of this nadir in bone marrow counts caused by cyclophosphamide (FIG. 2B). Thus, vaso reduced significantly bone marrow toxicity by cyclophosphamide.

The bone marrow from mice treated with cyclophosphamide (2 mg/mouse) alone 5 days earlier showed a clear reduction in cellularity compared to the marrow from control untreated mice. However, the bone marrow from mice similarly treated with cyclophosphamine (2 mg/mouse) in conjunction with vasostatin was indistinguishable from that of control mice that had not been treated with cyclophosphamide.

Figure 3:
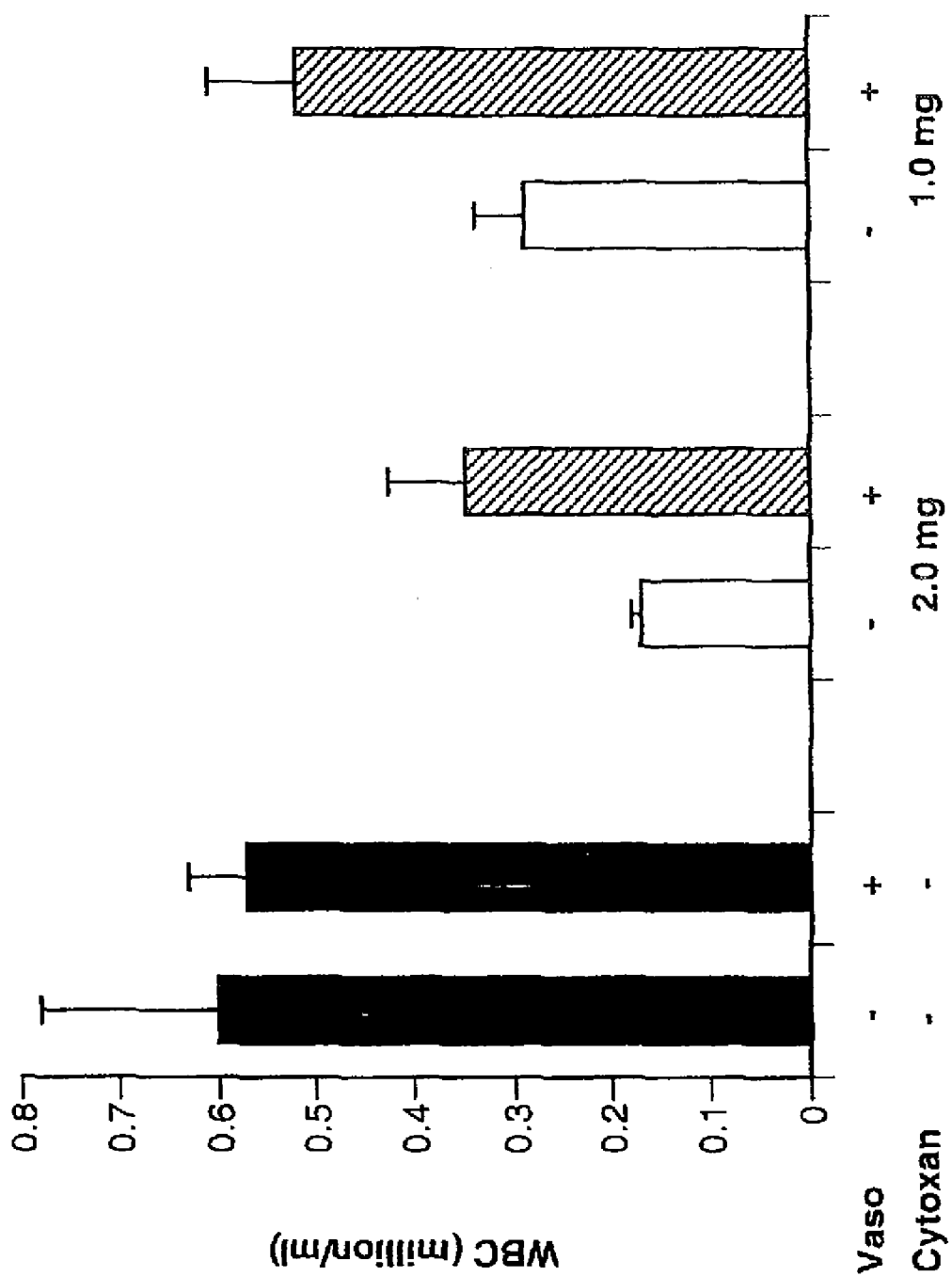
FIG. 3 is a bar graph of the effects of vaso on peripheral blood white cell counts after administration of cytoxan. Mice (C57BL/B6, females, 7.5 weeks old) were treated for 1 week with daily inoculations of vaso (300 µg/mouse) or buffer alone. On day 8, the mice received cytoxan (1 or 2 mg/mouse) and continued daily inoculation with buffer or vaso. Peripheral blood white cell counts were measured on day 5 after administration of cytoxan.

A reduction in the number of bone marrow cells is expected to translate into a reduction in peripheral blood counts. We therefore examined white blood cell counts in mice treated with cyclophosphamide alone or with vasostatin. On day 5 after administration of cyclophosphamide, peripheral blood white cell counts were significantly reduced when compared to the control mice that had received either buffer alone or vaso alone (FIG. 3). Importantly, this reduction in peripheral blood white cell counts caused by cyclophosphamide (2.0 or 1.0 mg/mouse) was alleviated by the administration of vaso (FIG. 3). Differential peripheral blood white blood cell counts revealed that the protective effect of vasostatin was attributable, in part, to an effect on cells of the neutrophil lineages. These results provide compelling evidence that vaso can protect bone marrow hematopoietic cells from cyclophosphamide induced toxicity.

Figure 14:
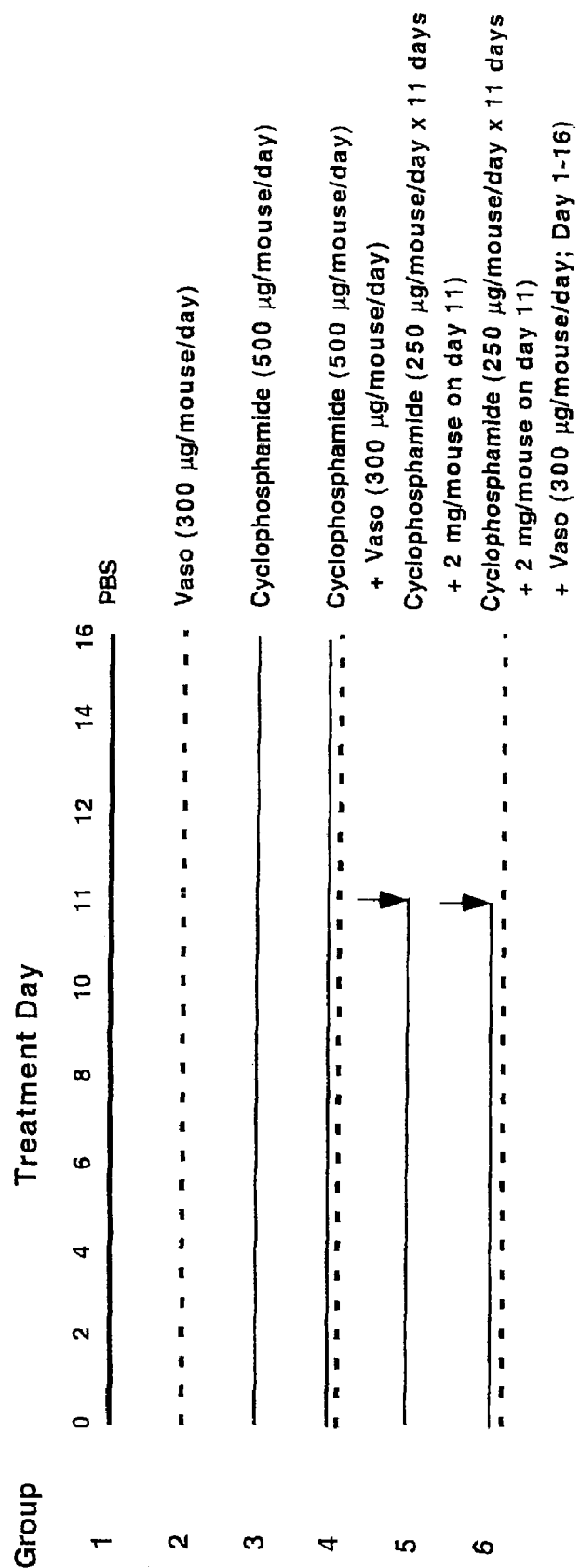
FIG. 14 is a schematic diagram of different treatment groups used in the studies described herein.
Group 1: Buffer alone (100 µl/mouse/day s.c)×16 days
Group 2: Vaso alone (300 µg/mouse/day s.c)×16 days
Group 3: Cyclophosphamide (500 µg/mouse/day i.p.)×16 days Group 4: Cyclophosphamide (500 µg/mouse/day i.p.)×16 days plus vaso (300 µg/mouse/day s.c)×16 days Group 5: Cyclophosphamide (250 µg/mouse/day i.p.)×11 days plus Cyclophosphamide 2 mg/mouse i.p. on day 11 Group 6: Cyclophosphamide (250 µg/mouse/day i.p.)×11 days plus Cyclophosphamide 2 mg/mouse i.p. on day 11 plus vaso (300 µg/mouse/day s.c) days 1-16.

In another experiment, the protective effect of vaso was tested when the bone marrow is exposed to protracted toxicity, rather than acute toxicity as described above. In addition, rather than treating the mice with vaso prior to toxin exposure as described above, mice were simultaneously inoculated with cyclophosphamide and vaso. Thus, groups of mice (n=6) received either buffer alone (100 μl s.c) daily for 16 days, vaso (300 μg/mouse s.c) alone daily for 16 days, cyclophosphamide (500 μg/mouse i.p.) either alone or together with vaso (300 μg/mouse s.c) for 16 days. Other groups of mice (n=6) were inoculated daily for 11 days with cyclophosphamide (250 μg/mouse i.p.) either alone or together with vaso (300 μg/mouse s.c). On day 11, all mice received an injection of cyclophosphamide (2.0 mg/mouse i.p.); those mice that had received vaso with cyclophosphamide (250 μg/mouse) continued treatment with vaso daily at the same dose (300 μg/mouse s.c) for 5 additional day (FIG. 14).

Figure 4A:
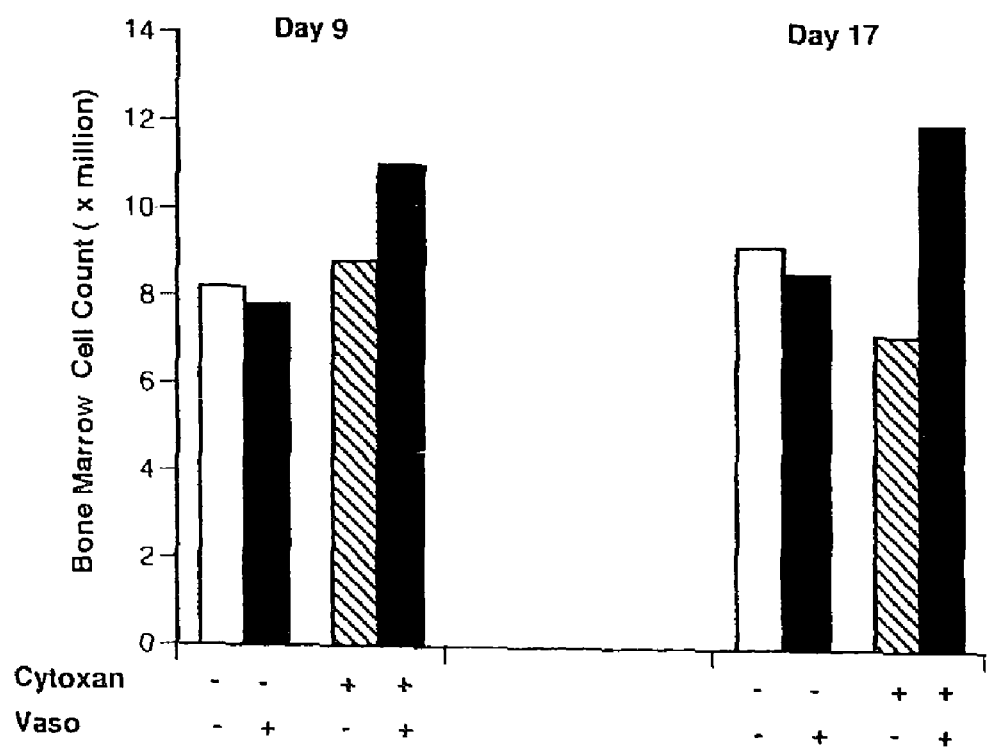
FIG. 4A is a bar graph of the bone marrow cell count from mice treated for 16 days with either buffer alone (PBS, 100 µl/mouse/day s.c), Vaso (300 µg/mouse/day s.c) alone, Cytoxan (500 µg/mouse/day i.p.) alone, or vaso (300 µg/mouse/day s.c) plus Cytoxan (500 µg/mouse/day i.p.). Bone marrow was harvested on days 9 and 17 and the number of nucleated cells were counted.
Figure 9:
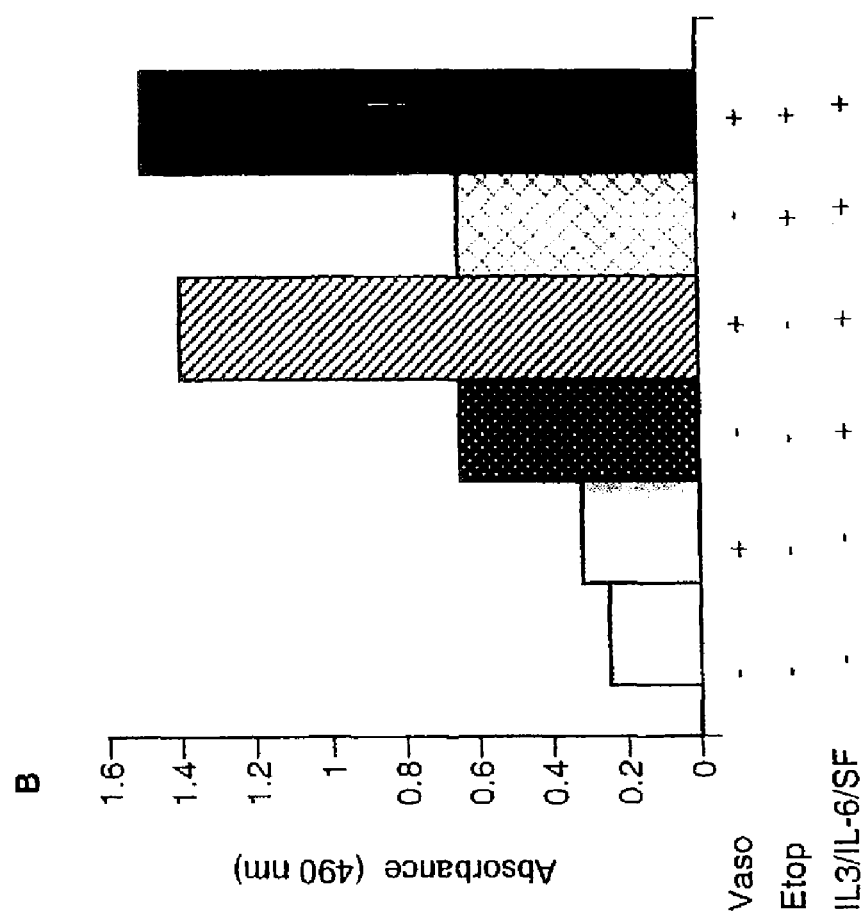
FIG. 9 is a series of bar graphs showing that vaso increases bone marrow cell proliferation in vitro. Bone marrow cells populations, obtained from the femural cavities of C57BL/6NCR mice (8 weeks of age), were cultured in culture medium alone or in medium supplemented with a mixture of IL-3 (20 ng/ml), IL-6 (100 ng/ml) and Stem Cell Factor (SF, 100 ng/ml). Vaso was added to the indicated cultures at 10 µg/ml; etoposide was added at the concentration of 77 nM.

As shown in FIG. 4A, 9 and 16-day treatment with cytoxan (500 μg/mouse/day) did not reduce bone marrow cell counts on day 9 but reduced them on day 17 compared to control mice that had been treated with PBS alone. In addition, vaso (300 μg/mouse/day s.c) administered alone to the mice had minimal effects on bone marrow cell counts on days 9 or 17. When the mice were treated with cyclophosphamide plus vasostatin, the bone marrow cell count on days 9 and 17 was higher than in the control mice and in the mice treated with cytoxan. Thus, vasostatin stimulated the proliferation of bone marrow cells in the presence of cytoxan and was fully protective of bone marrow toxicity following prolonged treatment with cyclophosphamide.

Figure 4B:
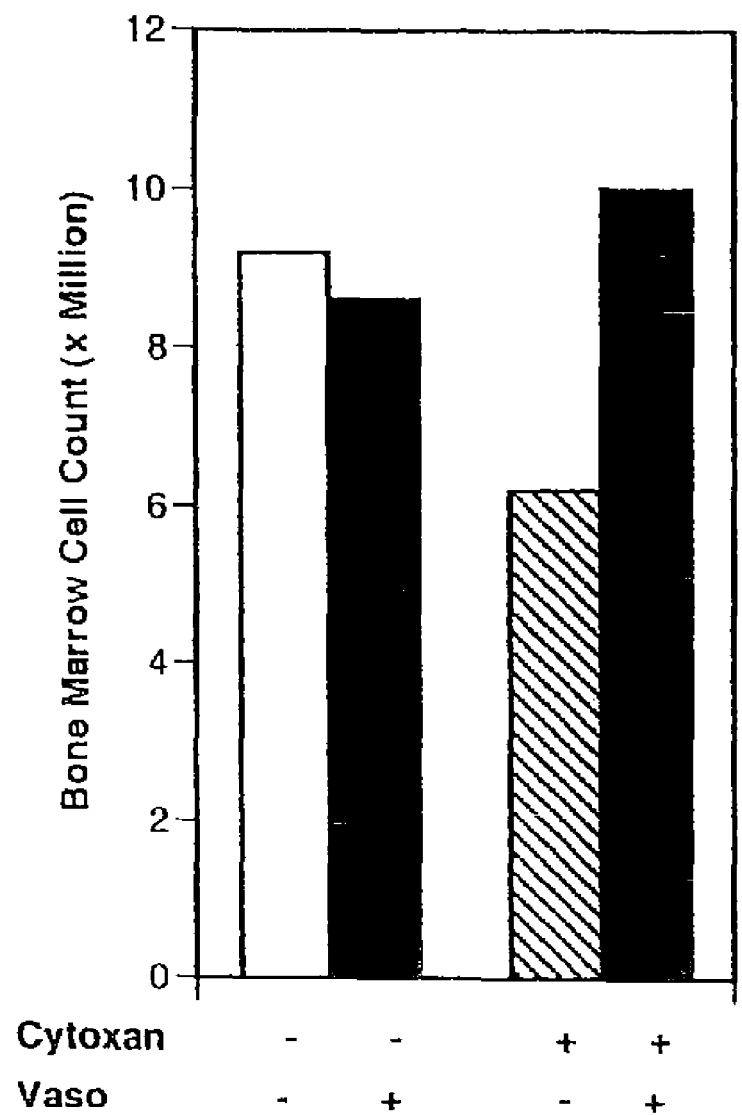
FIG. 4B is a bar graph of the bone marrow cell count from mice treated with for 11 days with either buffer alone (PBS, 100 µl/mouse/day s.c), Vaso (300 µg/mouse/day s.c) alone, Cytoxan (250 µg/mouse/day i.p.)×11 days plus Cytoxan 2 mg/mouse i.p. on day 11, or Cytoxan (250 µg/mouse/day i.p.)×11 days plus Cytoxan 2 mg/mouse i.p. on day 11 plus Vaso (300 µg/mouse/day s.c, days 1-16). Bone marrow cell counts were obtained on day 17.

Daily treatment with cyclophosphamide (250 μg/mouse/daily) was also performed for 11 days followed by 1 single injection of 2 mg cyclophosphamide/mouse on day 12. In this treatment series, considerable reduction of bone marrow cell counts was noted on day 17 (FIG. 4B). By contrast, Vaso (300 μg/mouse/day s.c) given daily to mice for 16 days in conjunction with cyclophosphamide (250 μg/mouse/daily for 11 days followed by 1 single injection of 2 mg cyclophosphamide/mouse on day 12), prevented the occurrence of a reduction in bone marrow cell counts on day 17. This time point corresponds to day 5 after the bolus cyclophosphamide (2 mg/mouse) injection, when maximal toxicity is expected from administration of cyclophosphamide. Indeed, bone marrow cell counts in these animals that had received both cytoxan and vaso were significantly higher than in the control mice that had received buffer alone (FIG. 4B).

Figure 4C:
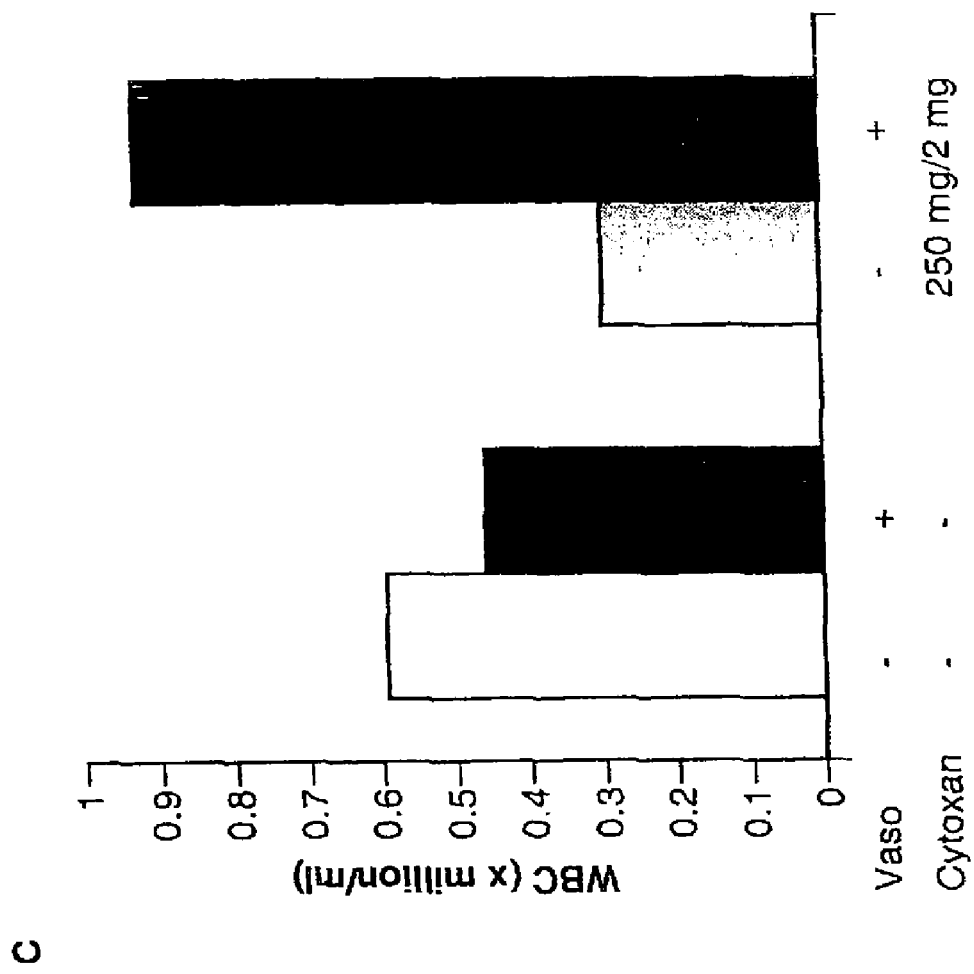
FIG. 4C is a bar graph of peripheral blood white cells counts (WBC) on day 17 from mice from the same treatment groups described in B.

Peripheral blood counts obtained on day 17 revealed a reduction in white blood cell counts in mice treated with cyclophosphamide (250 μg/mouse/daily) for 11 days followed by 1 single injection of 2 mg cyclophosphamide/mouse on day 12 compared to the untreated controls. Vaso, given alone, had minimal effects on peripheral white cell counts. Animals treated with vaso in conjunction with this regimen of cyclophosphamide displayed a significantly greater number of white blood cells in the circulation. Indeed, in this treatment group, peripheral blood cell counts were higher than in the normal controls that had been treated with buffer alone (FIG. 4C).

In the controls, the percent neutrophils ranged between 10 and 17%, and the percent lymphocytes ranged between 72 an 83%. In mice treated with cyclophosphamide (250 μg/mouse/daily for 11 days followed by 1 single injection of 2 mg cyclophosphamide/mouse on day 12) the average percent neutrophils on day 17 was 13.4% and the average percent lymphocytes was 62%. However, in mice treated with the same dose and regimen of cyclophosphamide plus vaso, the average percent neutrophils on day 17 was 63% and the average percent lymphocytes was 25%. Thus, differential peripheral blood counts revealed that vaso targeted predominantly the neutrophil series. Taken together, the results of this experiment demonstrate that vaso protects from the hematological toxicity derived from long-term treatment with cyclophosphamide. The results also demonstrate that this protective effect does not require that vaso be administered prior to institution of cytotoxic chemotherapy. Indeed, the concomitant administration of cytotoxic drug and vaso is effective at reducing toxicity to the hematopoietic department.

Example 3

Effects of Denaturing on the Activity of Vaso

To examine whether the effects of vaso on the hematopoietic system are attributable to the native protein, the effects of native vaso were compared with the effects of vaso that had been denatured by boiling. Groups of mice (n=10) were treated for 4 days with either buffer (100 μl/mouse s.c); native vaso (200 μg/mouse/day s.c); or denatured vaso (300 μg/mouse/day s.c). On day 5, some of the mice were injected with cyclophosphamide (2 mg/mouse/i.p.) and treatment continued with either buffer, native vaso or denatured vaso. The experiment was terminated on day 5, at which time peripheral blood counts were measured.

Figure 5:
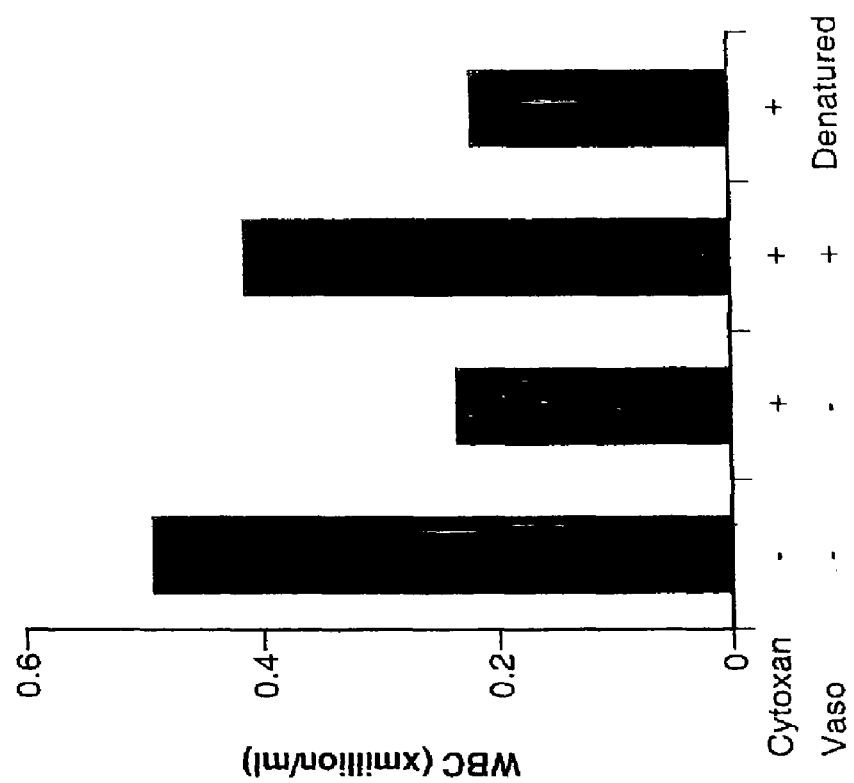
FIG. 5 is a bar graph showing differential effects of native and denatured vaso on hematopoiesis. Groups of mice (C57BL/B6, 6 weeks old, 10 mice/group) were treated for 4 days with either buffer (PBS, 100 µl/mouse/day), native vaso (200 µg/mouse/day s.c) or denatured vaso (PBS, 100 µl/mouse/day). On day 5, some of the animals were treated with cytoxan and the original treatment with buffer, native or denatured vaso was continued. On day 9 (5 days after one half of the mice had received cytoxan), peripheral blood white cell counts were measured.

As noted (FIG. 5), peripheral blood white cell counts from animals treated with cyclophosphamide were markedly reduced compared to the control mice treated with buffer alone. In addition, peripheral white cell counts from mice treated with cyclophosphamide plus native vaso were minimally different from those of the control mice that had not received cyclophosphamide. By contrast, denatured vaso was not effective at alleviating cyclophosphamide toxicity as revealed by peripheral blood white cell counts. These results demonstrate that native vaso (or active fragments or variants) mediates protection of chemotherapy-induced hematological toxicity.

Example 4

In Vivo Protection of Hematopoietic Stem Cells from Radiation-Induced Toxicity

Over a wide number of experiments, it was observed that BALB/c nu/nu mice irradiated with 400-450 rad and subsequently injected s.c. with human tumor cells lines, appeared healthier when they were treated with vaso than when they were treated with the buffer control. This healthier appearance was due, in part, to the larger weight of mice treated with vaso compared to the controls.

To examine this further, 7 week old BALB/c nu/nu mice were first irradiated with 400 rad. After 24 hr, the mice were incoculated s.c. with the human Burkitt lymphoma cell line CA46. One group of mice (n=12) was treated s.c. with the control protein maltose binding protein (MBP, 40 μg/mouse/day), whereas another group (n=12) was treated s.c. with MBP-vaso (60 μg/mouse/day). Some of the mice from each group were killed on day 15, whereas the other mice were kept for up to 2.5 months.

Tumor size and weight was then analyzed in all groups of mice. Tumor size and weight measurements confirmed that vasostatin has anti-tumor effects. Specifically, tumor size and weight in animals treated with MBP were 1.23 $cm^2$ and 0.433 g, respectively; whereas tumor size and weight of tumors from mice treated with vaso were 0.67 $cm^2$ and 0.22 g. Histological examination of the femural bone marrow from each of the groups revealed that the bone marrow from mice that had received 400 rad total body irradiation and were subsequently treated with MBP showed a reduced cellularity involving all lineages of hematopoietic cells. This is in contrast to the bone marrow from mice that had received a similar dose of irradiation and were subsequently treated with MBP-vaso.

It is known that the DNA-damaging effects of irradiation occur over a period of days after the radiation insult has occurred, at the time when DNA replication occurs. Thus, these results provided evidence that vaso can protect the hematopoietic tissue from radiation-induced toxicity. This protective effect of vaso is operative even after irradiation has already occurred, and does not interfere with the previously demonstrated anti-tumor effect of vaso.

In a subsequent experiment, groups of 8 week old C57BL/6N mice were irradiated with either 300 or 400 rad total body irradiation and treated the mice daily with s.c. inoculations of either buffer of vaso (300 μg/mouse/day). Peripheral white blood cell counts were obtained on days 5 and 9 post irradiation. On day 5, the total white cell count in the mice that had received 300 rad total body irradiation and had been treated with buffer was $1.2 \times 10^3/mm^3$ as opposed to $2.14 \times 10^3/mm^3$ in the mice treated with vaso. Also on day 5 post-irradiation, the total white cell count in the mice that had received 400 rad total body irradiation and had been treated with buffer was $0.66 \times 10^3/mm^3$ as opposed to $1.22 \times 10^3/mm^3$ in the mice treated with vaso. On day 9 post irradiation, the total white cell count in the mice that had received 400 rad total body irradiation and had been treated with buffer was $0.79 \times 10^3/mm^3$ as opposed to $1.37 \times 10^3/mm^3$ in the mice treated with vaso. These results demonstrate vaso can provide protection from radiation-induced toxicity to the hematopoietic tissue.

Example 5

Effects of Vasostatin on Bone Marrow Cell Proliferation In Vitro

The foregoing examples indicate that vasostatin has effects on bone marrow hematopoietic cells. To assess this further, the effects of vasostatin were examined on bone marrow-derived cells in vitro.

Figure 6B:
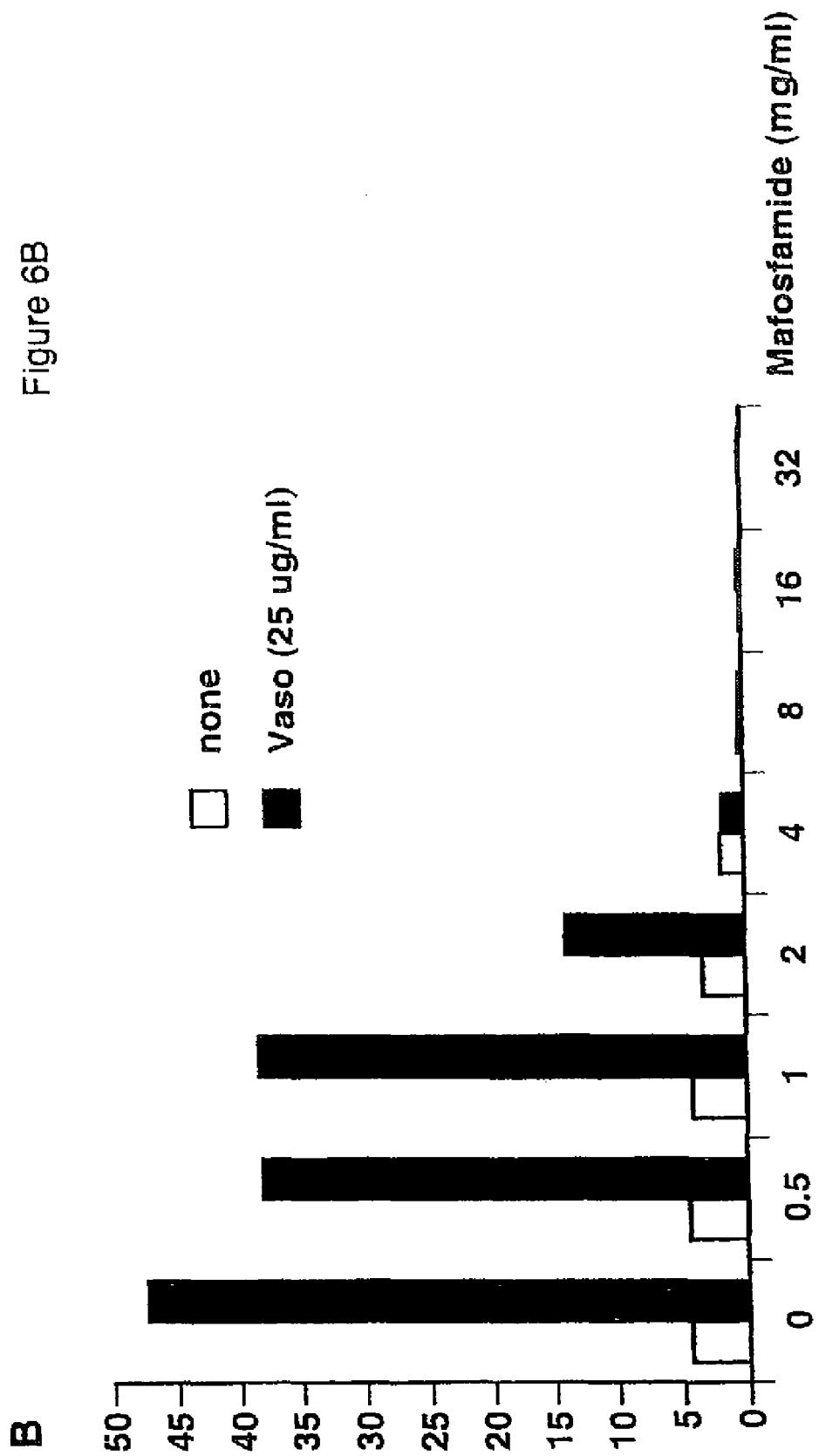
FIG. 6B is a bar graph showing bone marrow cell proliferation after 6 days culture with Mafosfamide at varying concentrations (0.5-32 µg/ml) with or without growth factors (IL-3 plus IL-6 plus Stem Cell Factor) and vaso (12.5 µg/ml).

Murine bone marrow cells were obtained from the femurs of C57BL/6 mice (age 6 months) by flushing the bone cavity with phosphate buffer saline. Pooled bone marrow cells from different femurs were depleted of red cells, washed, and suspended in culture medium (DMEM supplemented with 15% FCS). Bone marrow-derived cells were cultured ($1 \times 10^6$/ml; DMEM medium with 15% FCS) in 24-well tissue culture wells with either a mixture of growth factors (murine IL-3, 20 ng/ml; murine IL-6, 100 ng/ml; murine stem cell factor, 100 ng) alone or with growth factors plus vaso at varying concentrations (12.5-50 μg/ml). After 5 days culture, cell proliferation was measured by transferring equal volumes (0.2 ml) of bone marrow cultures to microtiter wells and pulsing with [$^3$H] thymidine overnight. On day 5 (FIG. 6A), bone marrow cells displayed low-level proliferation in response to the growth factor mixture alone. However, bone marrow cell proliferation was 21-54 fold higher when vaso was added to the growth factor mixture (IL-3 plus, IL-6, plus Stem Cell Factor) compared to addition of theses growth factors alone.

Mafosfamide, the active metabolite of cyclophosphamide, was added to the bone marrow cultures supplemented with growth factors (murine IL-3 20 ng/ml; murine IL-6 100 ng/ml; murine stem cell factor 100 ng/ml) alone or in conjunction with vaso (12.5-50 μg/ml). Mafosfamide was added either at the time the cultures were first established or after 3 days incubation. Cell proliferation was measured after 6 days of culture. Mafosfamide dose-dependently inhibited bone marrow cell proliferation when added either at time 0 (FIG. 6B) or after 3 days. Importantly, vaso (12.5 μg/ml) markedly enhanced the proliferation of bone marrow cells exposed to mafosfamide.

When mafosfamide was added at time 0, the growth stimulatory effects of vaso were appreciable at mafosfamide concentrations ranging between 0.5 and 2 μg/ml, whereas when mafosfamide was added after 3 days of culture, the effect was appreciable at mafosfamide concentrations as high as 8 μg/ml (not shown). Vaso can therefore stimulate the proliferation of murine bone marrow cells in culture even in the presence of mafosfamide.

In an additional experiment, the effects of vaso on bone marrow cell proliferation were analyzed in the presence of methotrexate. Bone marrow cell suspensions were obtained from femurs of C57BL/6NCR mice (3.5 months old) and cultured (24 well plates, $1 \times 10^6$ cell/ml) in culture medium (DMEM with 15% FCS) alone or supplemented with growth factors (murine IL-3, 20 ng/ml; murine IL-6, 100 ng/ml; murine stem cell factor, 100 ng) with or without vaso (0.25-10 μg/ml). Denatured vaso was also used as a control. Proliferation was measured by [$^3$H] thymidine incorporation during the final 24 hr of a 7 day culture (FIG. 7A).

In the absence of exogenously added growth factors, vaso at the highest concentration used (10 μg/ml) had low level stimulatory effect (approximately 2-fold stimulation of background cpm). Methotrexate markedly reduced the proliferation of bone marrow cells stimulated with growth factors, presumably due to its toxic effects. By contrast, vaso dose-dependently stimulated bone marrow cell proliferation in the presence of methotrexate (100 nM) and the growth factors. This increase in cell proliferation by vaso, as detected by [$^3$H] thymidine incorporation, was associated with an increase in the number of living bone marrow cells detected in culture (FIG. 7B), as assessed by the conversion of Owen's reagent into a colored formazan product measured by absorbance at 490 nM (One Solution Reagent, Promega, Madison. Wis.).

Figure 8A:
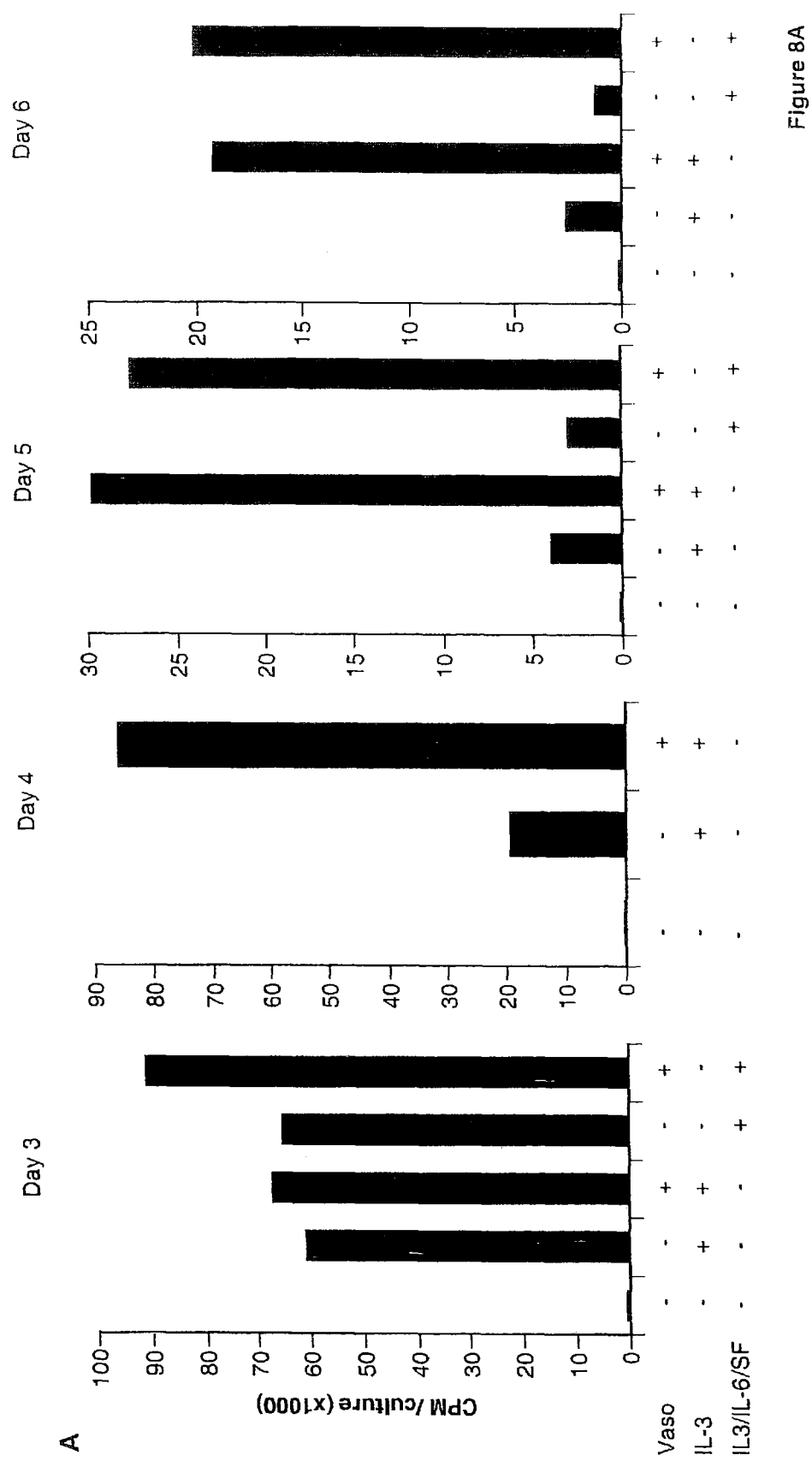
FIG. 8A is a bar graph showing the effects of vaso on bone marrow cell proliferation to IL-3 or to the combination of IL-3, IL-6 and Stem Cell factor.
Figure 8B:
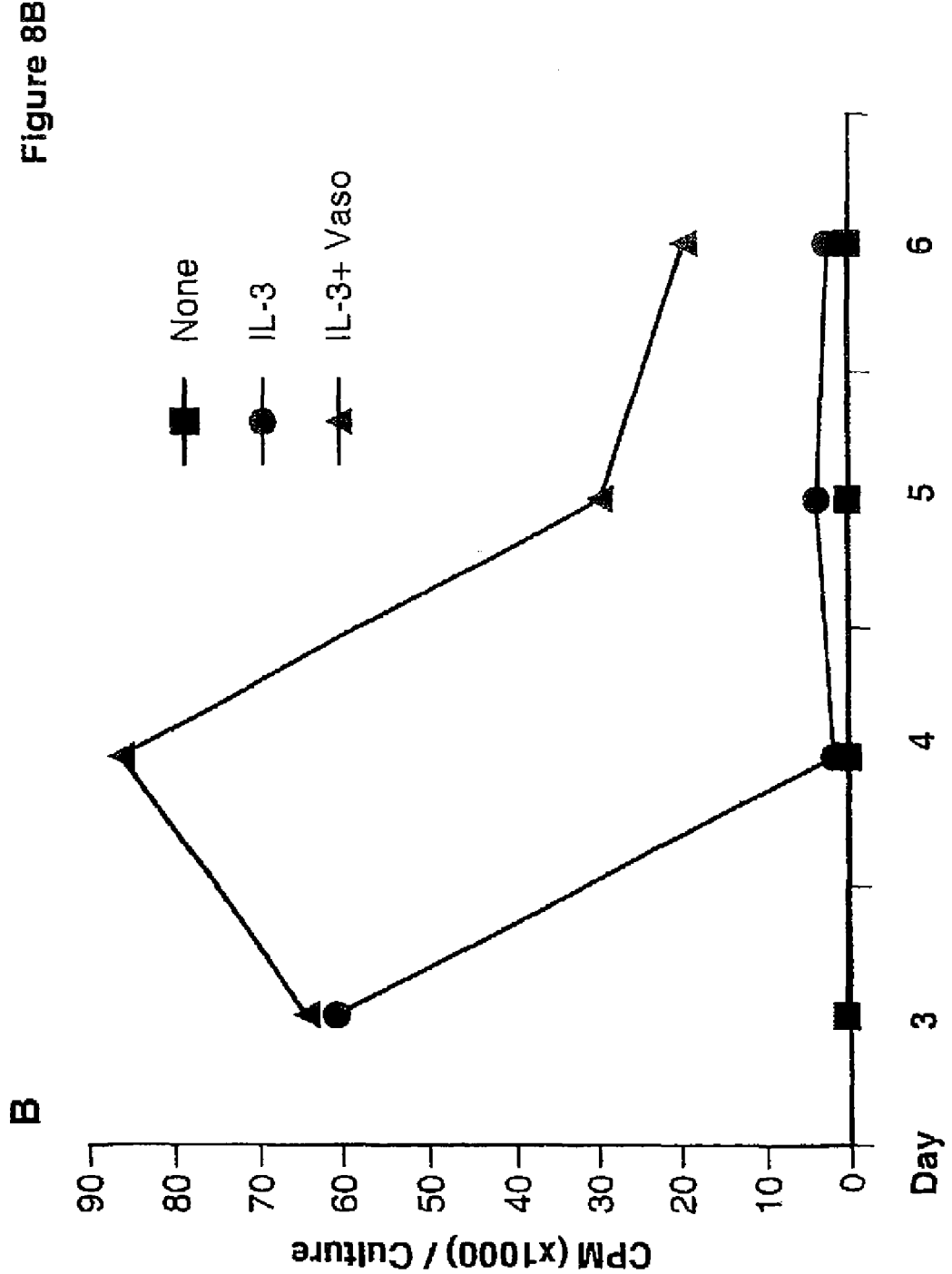
FIG. 8B is a graph showing the kinetics of bone marrow cell proliferation in response to IL-3 alone or with vaso.

The time course of vaso-induced stimulation of bone marrow cell growth was examined in detail. In addition, the effects of vaso on bone marrow cells cultured with the combination of growth factors used above (murine IL-3, 20 ng/ml plus murine IL-6, 100 ng/ml; plus murine Stem Cell Factor, 100 ng) was compared with the effect on bone marrow cells cultured with IL-3 (20 ng/ml) alone. On day 3, bone marrow cells proliferate vigorously to IL-3 or to the combination of IL-3, IL-6 and Stem Cell Factor (FIG. 8A). At this time-point (day 3), vaso (10 µg/ml) enhanced the response induced by the combination of IL-3, IL-6 and Stem Cell Factor slightly. By day 4, the proliferative bone marrow cell response to IL-3 was markedly reduced compared to day 3. However, vaso (10 µg/ml) enhanced by approximately 3-fold the IL-3 induced response such that no decline in proliferation was noticed between day 3 and 4. By day 5 or 6, the proliferative bone marrow responses to either IL-3 or the combination of IL-3, IL-6 and Stem Cell Factor was further reduced, and vaso enhanced this response by 7-16 fold. (FIG. 8A). Thus, vaso can promote the proliferation of bone marrow hematopoietic cells in conjunction with either IL-3 alone or a combination of growth factors that includes IL-3, IL-6 and Stem Cell Factor. Whereas bone marrow cells cultured with growth factors alone display an initial burst of proliferation followed by a steady and rapid decline, vaso sustains the proliferative response and shifts the curve of decline such that the cells continue to proliferate and survive for a longer time period (FIG. 8B).

As demonstrated above, it was determined that vaso could stimulate bone marrow cells exposed to the chemotherapeutic agents mafosfamide or methotrexate. The effects of vaso on the growth of bone marrow cells cultured in the presence of etoposide for 4, 5 or 6 days (FIG. 9A) was also examined. Murine bone marrow cells obtained from 8 week-old C57/BL6 mice were cultured in medium alone or in the presence of growth factors [murine IL-3 (20 ng/ml), plus murine IL-6 (100 ng/ml) plus murine stem cell factor (100 ng/ml)] with or without vaso (10 µg/ml) and etoposide (77 nM).

As shown (FIG. 9), vaso failed to directly stimulate the proliferation of murine bone marrow cells. However, in the presence of growth factors, vaso promoted bone marrow cell proliferation by 6.5-fold on day 4; 39-fold on day 5; and 17-fold on day 6. Etoposide added at a concentration of 77 nM reduced the proliferation of bone marrow cells in the presence of growth factors (IL-3, IL-4 and Stem Cell Factor) by 1.5-2.7 fold over the 6-day culture period. Vaso promoted bone marrow cell proliferation in the presence of Etoposide to the same or greater degree than in the absence of Etoposide (FIG. 9).

Stimulation of bone marrow cell proliferation by vaso was associated with an increased number of bone marrow cells, measured as absorbance from the conversion of Owen's reagent into a colored formazan product (One Solution Reagent, Promega, Madison. Wis.). Consistent with the results of proliferation assays, vaso added to medium alone increased only minimally the number of cells in culture. However, in the presence of growth factors (IL-3, IL-6 and Stem Cell Factor) either alone or with etoposide (77 nM), vaso increased significantly the number of cells counted after 5 days of culture (FIG. 9B). These experiments confirm that vaso markedly enhances the proliferation of murine bone marrow cells induced by growth factors. The results further show that this stimulatory effect of vaso persists in the presence of drugs such as etoposide used in culture at toxic concentrations.

In other experiments, the effect of a fixed dose of vaso (10 µg/ml) on the growth of murine marrow cells cultured was examined in the presence of various doses of the drugs Etoposide and Cisplatinum (cis-diammine-dichloroplatinum II). On day 5 of culture, the proliferation of bone marrow cells incubated with IL-3 alone (20 ng/ml) was inhibited to varying degrees by Etoposide at concentrations ranging between 1425 and 15.4 nM (FIG. 10A). Vaso (10 µg/ml) enhanced bone marrow cell proliferation induced by IL-3 (20 ng/ml). This increase of IL-3-induce bone marrow proliferation by vaso was evident even in the presence of Etoposide (385-15.4 nM). However, at the highest dose of Etoposide tested (1425 nM) virtually no proliferation was measured with IL-3 alone or in conjunction with vaso, suggesting that irreversible cell toxicity had occurred.

Figure 10B:
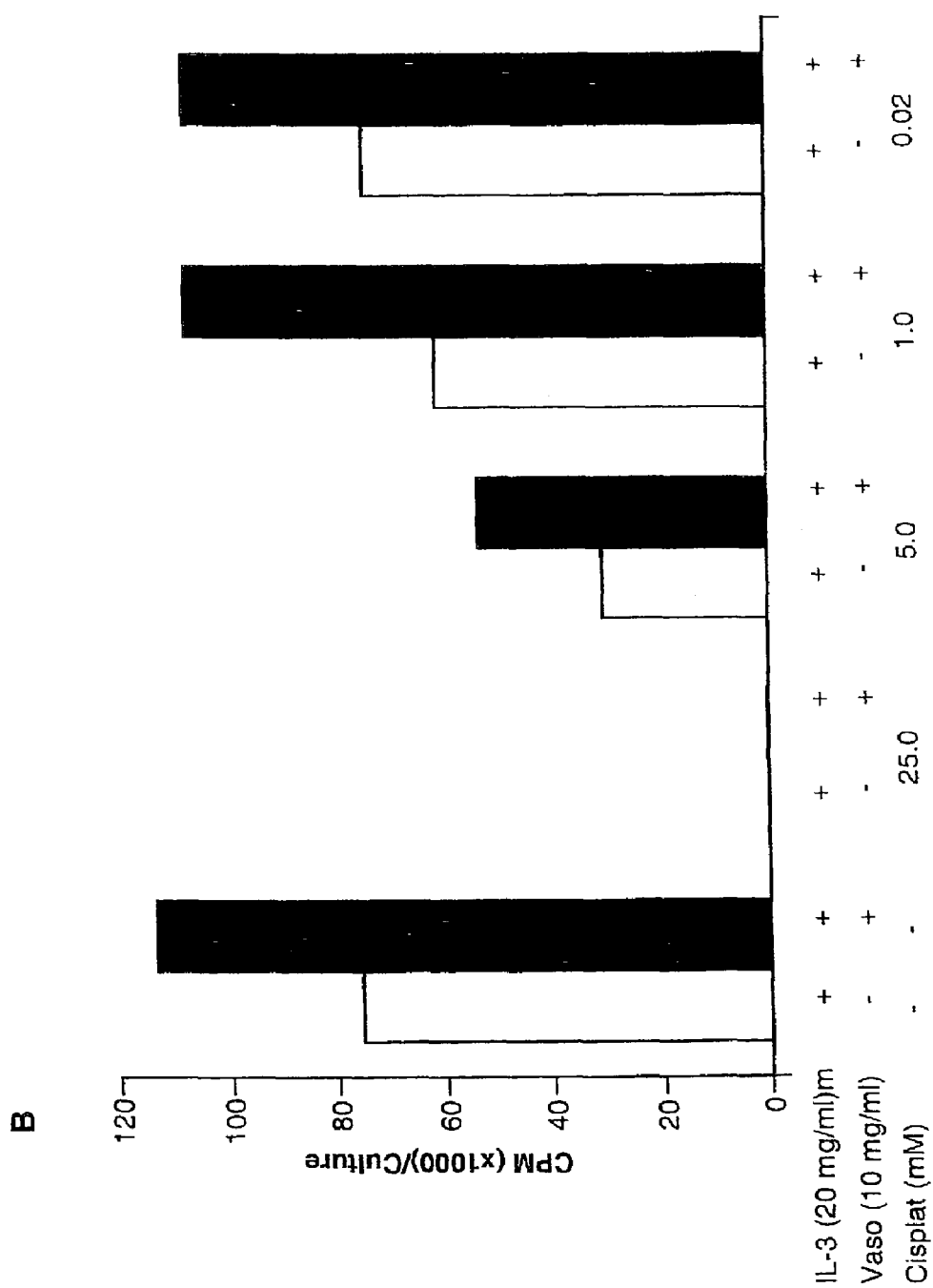
FIG. 10B is a bar graph when cisplatin (cisplat) was added to the IL-3 supplemented cultures at concentrations ranging between 0.02 and 25 µM. Cell proliferation was measured on day 5 of culture by $^3$H thymidine incorporation. Means of triplicate cultures.

Similar results were noted with Cisplatinum (25-0.2 µM). Vaso (10 µg/ml) enhanced murine bone marrow cell proliferation in the presence of IL-3 (30 µg/ml) with or without cisplatinum at concentrations ranging between 5 and 0.02 nM. However, at the highest dose tested (25 µM), bone marrow cell proliferation induced by IL-3 was minimal, regardless the addition of vaso (FIG. 10B).

Together, these results document that vaso enhances growth-factor induced growth of murine bone marrow cells. They further demonstrate that bone marrow cell stimulation by vaso is observed also in the presence of chemotherapeutic agents that are toxic for bone marrow cells. Thus, vaso is a growth/survival factor for murine hematopoietic cells which can protect these cells from toxicity. The toxic agents used in these examples included maphosphamide, a cross-linker of DNA, methotrexate, an antimetabolite that inhibits dihydrofolic acid reductase, etoposide, an inhibitor of cell cycle progression, and cisplatin, a cell-cycle non-specific interstrand DNA crosslinker. Since efficacy was noted with all these agents, it is believed that vaso can protect bone marrow-derived hematopoietic cells from diverse types of toxins acting through diverse pathways.

Example 6

Characterization of Immature Hematopoietic Cells as Targets of Vaso-Induced Growth Stimulation The examples described above utilized unpurified populations of murine bone marrow cells derived from the femur. To characterize the cell or cells within the bone marrow cell population that are targets of stimulation by vaso, cell separation experiments were performed. Enrichment of murine hematopoietic progenitors in conjunction with the removal of lineage-committed cells was achieved by incubating the cells with a cocktail of biotinylated monoclonal antibodies directed at CD5, CD45R (B220), CD11b (Mac-1), Myeloid Differentiation Antigen (Gr-1) and Erythroid cells (TERI 19), followed by magnetic cell depletion by StemSep™ protocol (Stem Cell Technologies). As described above, Lin⁻ cells are those cells that do not express a lineage specific marker. The resulting negatively-selected cell population is enriched with hematopoietic progenitors, as defined by in vitro and in vivo assays.

Figure 11:
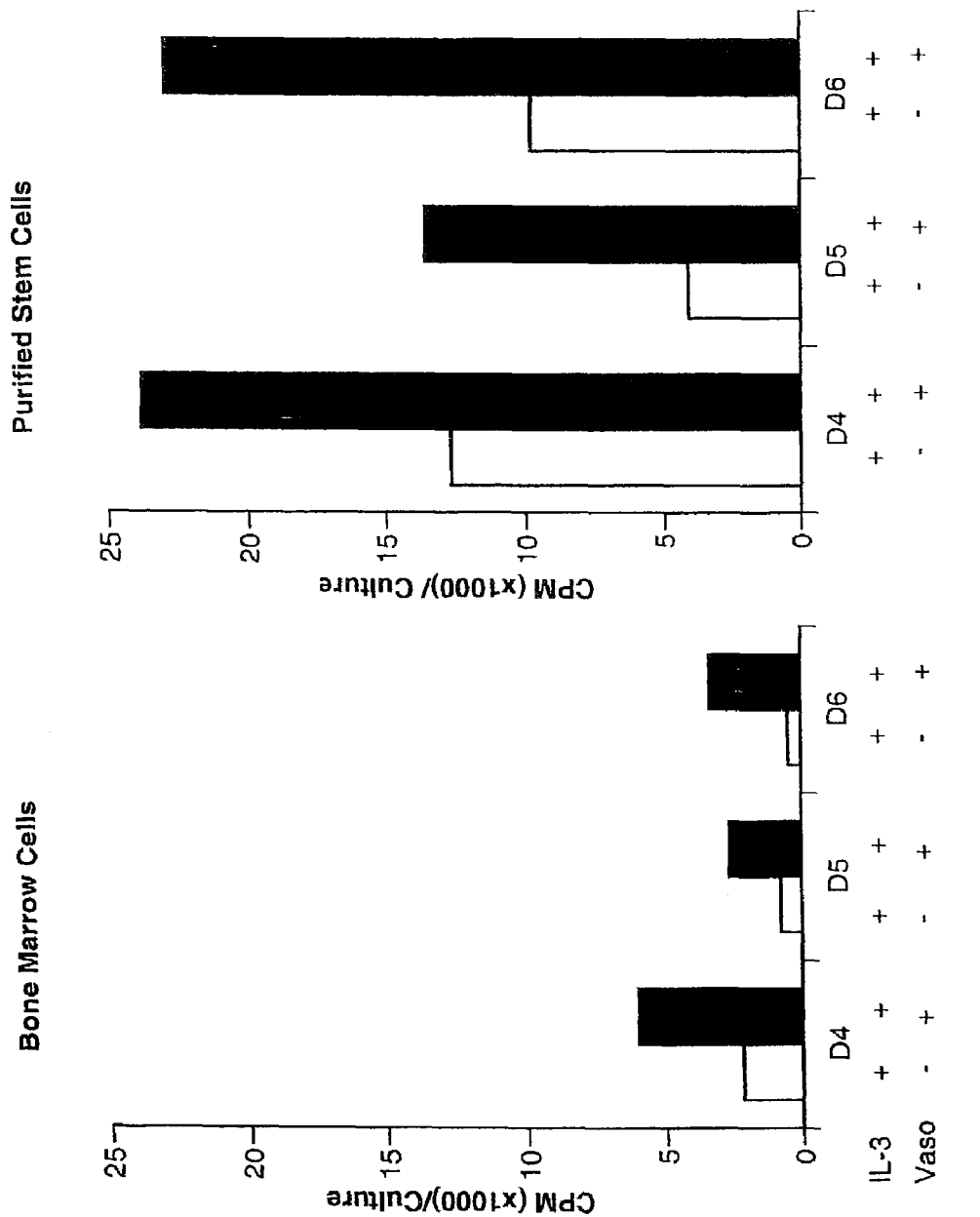
FIG. 11 is a set of two bar graphs showing the proliferative responses of unseparated (FIG. 11A) and purified (FIG. 11B) bone marrow cell populations in response to vaso. Bone marrow cell populations, obtained from the femural cavities of C57BL/6NCR mice (9 weeks of age) were either used as such or were further purified by negative selection as lineage negative (CD5, CD45R, CD11b, Gr-1 and TER119) cells by magnetic cell depletion. Both cell populations were incubated (0.5×10$^6$ cells/ml) in culture medium supplemented with IL-3 (20 ng/ml) with or without vaso (10 µg/ml). Cell proliferation was measured by $^3$H thymidine incorporation during the final 22 hr of a 4, 5 or 6-day (D) culture. Data shown reflects the mean of triplicate cultures.

The effects of vaso were tested on this cell population that is enriched with murine hematopoietic cells, and compared with unseparated bone marrow populations. Thus, unseparated or hematopoietic-cell enriched bone marrow populations were cultured ($0.5 \times 10^6$ cells/ml) in 24 well plates in culture medium containing murine IL-3 (20 ng/ml) with our without vaso (10 µg/ml). On days 4 and 5, cell proliferation was measured. At those time-points (FIG. 11), the unseparated marrow as well as the enriched bone marrow responded to vaso with increased proliferation. On day 5, the observed increase in cell proliferation induced by vaso was 3.3 fold with enriched marrow and 3.4 fold with unseparated marrow. The similarity in the degree of cell stimulation by vaso strongly supports the notion that the target cell or cells for vaso stimulation is included in the negatively purified cell population that is enriched with hematopoietic cells. This further demonstrates that immature hematopoietic cells are targets for growth stimulation by vaso.

Example 7

Effects of Vaso on Human Hematopoietic Cells

Since the examples above indicated that immature hematopoietic cells are targets for growth stimulation by vaso, human hematopoietic cells were examined which had been derived from the peripheral blood of donors mobilized with G-CSF as previously described (Demirer et al., 1999; To et al., 1997). To this end, CD34+ cells were purified to a high degree of homogeneity (>90% purity) from the peripheral blood of normal donors, according to established protocols (Mavroudis et al. Bone Marrow Transplant 21:431-40, 1998).

The purified human CD34+ cells along with the negatively selected CD34- mononuclear cell population were cultured in RPMI 1640 medium containing 15% FBS. Human Stem Cell Factor (300 ng/ml) and Flt-3 ligand (300 ng/ml) were added to the culture medium. As shown (FIG. 12), the purified human peripheral blood CD34+ cells responded with increased proliferation to vaso (10 μg/ml). By contrast, the negatively selected CD34- cell population proliferated minimally in response to the growth factors Stem Cell Factor and Flt-3 ligand alone or in conjunction with vaso. These results demonstrate that human hematopoietic cells within the selected CD34+ cell population can respond with increased cell proliferation in response to vaso. Thus, purified hematopoietic cells from both mouse and man proliferate in response to vaso.

Example 8

Characterization of the Active Site for Stimulation of Hematopoietic Cells

Vaso represents the 1-180 amino acid N-terminal fragment of calreticulin. In order to demonstrate that fragments of vaso are also active as stimulants of hematopoietic cell growth, deletion mutants of vaso were prepared as fusion proteins of Maltose Binding Protein (MBP) using the PET-2× vector (Promega), as previously described (Pike et al., 1998; Pike et al., 1999). In particular, three deletion mutants were informative: MBP-calreticulin fragment 103-163 (61 amino acid fragment, SEQ ID NO:4); MBP-calreticulin fragment 120-146 (27 amino acid fragment, SEQ ID NO:5); and MBP-calreticulin fragment 129-146 (18 amino acid fragment, SEQ ID NO:6). The cloning accuracy for each of the mutants was confirmed by DNA sequencing. The MBP-fusion proteins were purified to apparent homogeneity by affinity over amylose resin column, as previously described (Pike et al., 1998; Pike et al., 1999).

Figure 13A:
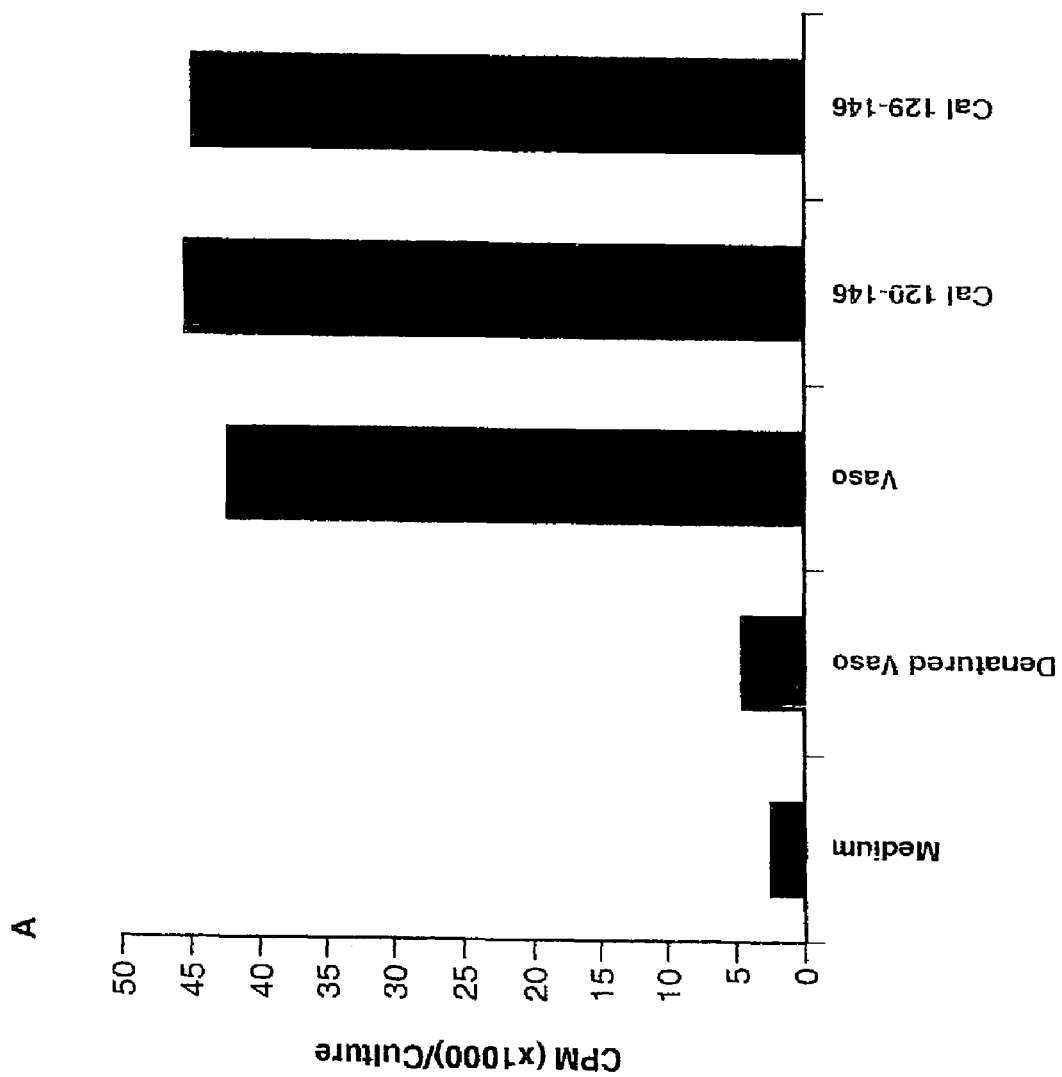
FIG. 13A shows the effects of vaso, denatured vaso, calreticulin fragment 120-146 and calreticulin fragment 129-146 (all at 10 µg/ml) on the 5-day proliferation of bone marrow cell populations in the presence of IL-3.
Figure 13B:
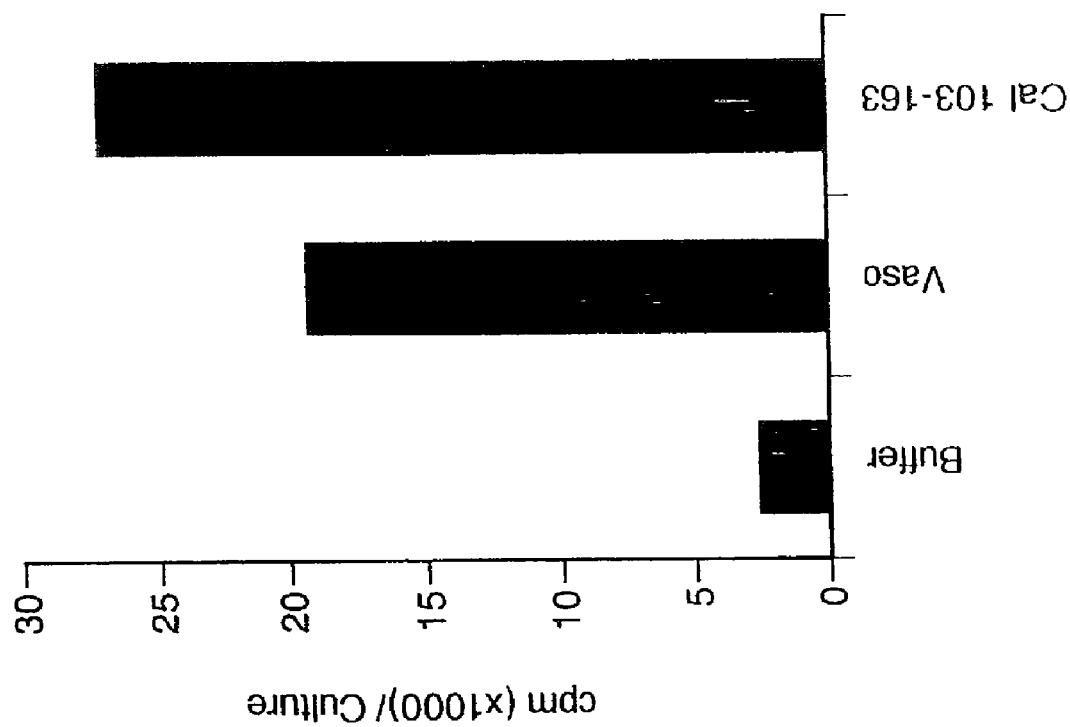
FIG. 13B is a bar graph of the effects of vaso and calreticulin fragment 103-163 (all at 10 µg/ml) on the 6-day proliferation of bone marrow cell populations in the presence of IL-3.

Vaso, calreticulin fragment 103-163, calreticulin fragment 120-146, and calreticulin fragment 128-146 (all used at 10 μg/ml) were tested in side-by-side assays for their ability to stimulate murine bone marrow hematopoietic cells in the presence of IL-3 (20 ng/ml). As shown in a representative experiment (FIGS. 13A, 13B) all these molecules, but not MBP-vaso that had been denatured, stimulated the growth of murine hematopoietic cells after 5 or 6 days of culture. In other experiments, murine bone marrow cells that had been enriched for hematopoietic cells by negative selection and purified populations of human CD34+ peripheral blood cells were also tested. Using these purified populations of hematopoietic cells, it was found that vaso, calreticulin fragment 103-163, calreticulin fragment 120-146, and calreticulin fragment 129-146 similarly stimulated cell growth in the presence of either IL-3 alone or IL-3 together with IL-6 and Stem Cell Factor. These results, together, indicate that within calreticulin there is an active site for stimulation of hematopoietic cells. This fragment includes, but is not limited to, a fragment encompassing from about amino acid 129 to about amino acid 163, a fragment encompassing from about amino acid 129 to about amino acid 146, a fragment encompassing from about amino acid 120 to about amino acid 146, and a fragment encompassing from about amino acid 103 to about amino acid 163. This Example provides a convenient assay for detecting other fragments of vaso that stimulate hematopoietic cells.

Example 9

Vaso is a Restricted Stimulator of Cell Growth

The observation that vaso and some of its active fragments can promote the growth of murine and human hematopoietic cells in conjunction with other growth factors prompted the testing of these proteins for growth stimulation of cells of various hematopoietic lineages.

Human mononuclear cells, and mononuclear cells enriched for B or T cells, were used in proliferation assays in the presence of phytohemagglutinin(Sigma), pokeweed mitogen (Sigma) or Epstein-Barr virus (B95-8 strain), as described previously (Tosato et al., 1988). The lymphoblastoid cell line VDS-0, the Burkitt cell lines CA46, BL41, KK124, Ag876, SHO (Cherney et al., 1997), the T-cell line Molt-4 (ATCC), the Hodgkin's lymphoma cell line Hs445 (ATCC); the prostate adenocarcinoma cell lines TSU-Prl (from A. Passaniti, NIH, Baltimore, Md.), Du145 (ATCC), and PC3 (ATCC), and the acute promyelocytic leukemia cell line HL60 (ATCC) were cultured in RPMI 1640 medium with 10% heat-inactivated FCS (BioWhittaker), 20 mM L-glutamine (Sigma) and 5 μg/ml gentamicin, and tested in 3-5 days proliferation assays at cell densities varying from 300 to 2400 cells/microwell. The neuroblastoma cell line SKNMC (ATCC) was cultured in EMEM medium BioWhittaker) with 10% heat inactivated FCS and gentamicin and tested for proliferation at 125-1000 cells/well. The lung adenocarcinoma cell line A549 (ATCC) was cultured in F-12 Nutrient Mixture (HAM, Gibco BRL) with 10% heat-inactivated FCS, gentamicin and tested for proliferation at 250-2000 cells/well. The breast adenocarcinoma MDA-MB-468 (ATCC) and the Wilms tumor SK-NEP-1 (ATCC) cell lines were cultured in Leibovitz L-15 medium (GIBCO, BRL) supplemented with 10% heat-inactivated FCS and gentamicin, and tested for proliferation at 300-2500 cells/well. The colon carcinoma cell line SW480 (ATCC), the melanoma cell line A-375 (ATCC), and human foreskin fibroblasts (H5 68, ATCC) were cultured in DMEM medium (BioWhittaker) with 10% heat-inactivated FCS and gentamicin, and were tested for proliferation at 500-5000 cells/well.

The results of these assays showed that, in contrast to its ability to stimulate the proliferation of primary cultures of bone marrow cells, vaso has minimal stimulatory (or inhibitory) effects on the proliferation of a variety of cell and cell lines, when tested in vitro at concentrations ranging between 0.25 and 50 μg/ml.

As previously reported, vaso consistently inhibited the proliferation of primary cultures of human umbilical vein-derived (HUVEC) and of fetal bovine heart endothelial cells (FBHEC) (Pike et al., 1998; Pike et al., 1999).

Thus, bone marrow-derived and peripheral blood derived hematopoietic cells are unusual in their ability to respond with increased proliferation to vaso and its active fragments.

Example 10

Administration of Therapeutically Effective Fragments of Vaso

In one embodiment, a method of treating a subject with a neoplastic disorder is provided. The method includes administering to the subject treated with a chemotherapeutic agent, or irradiation, vaso or a therapeutically effective fragment thereof. In another embodiment, the method includes administering to the subject treated with a chemotherapeutic agent, or irradiation, a therapeutic nucleic acid sequence that includes a promoter operably linked to a nucleic acid sequence encoding vaso or a therapeutically effective fragment thereof.

In one embodiment, a nucleic acid encoding vaso, or a therapeutically effective fragment thereof, is administered to a subject treated with chemotherapy or irradiation. The nucleic acid encoding vaso, or a therapeutically effective fragment thereof, can be operably linked to a promoter, such as a constitutive or inducible promoter. Specific, non-limiting examples of promoters or use are the CMV promoter, an immunoglobulin promoter, an MHC promoter, or an actin promoter.

For administration of nucleic acids molecules, various viral vectors can be utilized. These vectors include adenovirus, herpes virus, vaccinia, or an RNA virus such as a retrovirus. In one embodiment, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). When the subject is a human, a vector such as the gibbon ape leukemia virus (GaLV) can be utilized. A number of additional retroviral vectors can incorporate multiple genes. All of these vectors can transfer or incorporate a gene for a selectable marker so that transduced cells can be identified and generated. By inserting a nucleic acid sequence encoding vaso, or a therapeutically effective fragment thereof, into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the polynucleotide encoding the TS peptide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to Q2, PA317, and PA 12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for the therapeutic polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. One colloidal system of use is a liposome. Liposomes are artificial membrane vesicles that are useful as delivery vehicles in vitro and in vivo. It has been shown that large uni-lamellar vesicles (LUV), which range in size from 0.2-4.0 µm can encapsulate a substantial percentage of an aqueous buffer containing large macromolecules. RNA, DNA and intact virions can be encapsulated within the aqueous interior and be delivered to cells in a biologically active form (Fraley et al., 1981, *Trends Biochem. Sci.* 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al., *Biotechniques* 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidyl-glycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

The method disclosed herein involves administering to a subject a therapeutically effective dose of a pharmaceutical composition containing a therapeutically effective fragment of vasostatin and a pharmaceutically acceptable carrier. Administering the pharmaceutical composition may be accomplished by any means known to the skilled artisan. By subject is meant any mammal, including a human.

The pharmaceutical compositions comprising the therapeutic sequence (either polypeptide or nucleic acid) are preferably prepared and administered in dose units. Solid dose units are tablets, capsules and suppositories. For treatment of a subject, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions are in general administered topically, intravenously, intramuscularly, subcutaneously, intratumorally, orally or parenterally or as implants, but even rectal use is possible in principle. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. Various considerations are described, e.g., in Gilman et al., eds., *Goodman and Gilman: The Pharmacological Bases of Therapeutics,* 8th ed., Pergamon Press, 1990; and *Remington's Pharmaceutical Sciences,* 17th ed., Mack Publishing Co., Easton, Pa., 1990, each of which is herein incorporated by reference. The pharmaceutical compositions are suitable for use in a variety of drug delivery systems. For a brief review of present methods for drug delivery, see Langer, *Science* 249:1527-1533, 1990, which is incorporated herein by reference.

Pharmaceutical compositions that comprise a vaso polypeptide as described herein as an active ingredient will normally be formulated with an appropriate solid or liquid carrier, depending upon the particular mode of administration chosen. The pharmaceutically acceptable carriers and excipients of use are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, other proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate.

Other medicinal and pharmaceutical agents, including chemotherapeutic agents, also may be included.

The pharmaceutical compositions that comprise a therapeutically effective fragment of vaso will preferably be formulated in unit dosage form, suitable for individual administration of precise dosages. One possible unit dosage contains approximately 100 μg of protein. Effective doses of the therapeutic molecules will vary depending on the nature and severity of the condition to be treated, the age and condition of the patient and other clinical factors. Doses can also be selected that achieve tissue concentrations which have been shown to be effective in vitro. However, the final determination of the appropriate treatment regimen will be made by the attending clinician. Typically, the dose range will be from about 0.1 μg/kg body weight to about 100 mg/kg body weight. Other suitable ranges include doses of from about 1 μg/kg to 10 mg/kg body weight. Continuous infusion may also be appropriate.

The serum half-life of the administered vaso or fragment thereof can be extended in various ways, for instance, through formation of a complex with a monoclonal antibody. Such an antibody is usually directed to the vaso polypeptide at a site that does not materially impair its therapeutic activity (e.g. see U.S. Pat. No. 5,055,289). Alternately, the peptide can be conjugated to non-antigenic polymers, such as polyethylene glycol or related polyalkylene glycol moieties, to increase their serum persistence (see, for instance, Nieforth et al., (1996) and U.S. Pat. Nos. 5,681,811; 5,711,944; and 5,738,846), or to a carrier peptide, such as maltose binding protein, six histidine residues or gluthione-S-transferase.

The amount of active compound administered will be dependent on the subject being treated, the severity of the affliction, and the manner of administration, and the chemotherapy or irradiation being administered, and is best left to the judgment of the prescribing clinician. Within these bounds, the formulation to be administered will contain a quantity of the active component(s) in an amount effective to achieve the desired effect in the subject being treated. The particular mode of administration and the dosage regimen will be selected by the attending clinician, taking into account the particulars of the case (e.g., the patient, the disease, and the disease state, and the dosing strategy for the chemotherapeutic agent or irradiation involved). For instance, a specific tumor or cancer treatment typically involves daily or multi-daily doses of a chemotherapeutic agent a period of months or even years. Vaso or a therapeutically effective fragment thereof may be administered to humans, or other animals in various manners such as topically, orally, intravenously, intramuscularly, intraperitoneally, intranasally, intradermally, intrathecally, and subcutaneously. Administration of vaso or a therapeutically effective fragment thereof as a composition is indicated for patients with malignancies or neoplasms, whether or not immunosuppressed, a chemotherapeutic agent or irradiation is administered to the subject at a concentration that affects the bone marrow (in the absence of vaso or a fragment thereof).

As is known in the art, protein-based pharmaceuticals may be only inefficiently delivered through ingestion. However, pill-based forms of pharmaceutical proteins may be administered subcutaneously, particularly if formulated in a slow-release composition. Slow-release formulations may be produced by combining the target protein with a biocompatible matrix, such as cholesterol. Another possible method of administering protein pharmaceuticals is through the use of mini osmotic pumps. As stated above a biocompatible carrier would also be used in conjunction with this method of delivery.

The cell growth-regulating activity exhibited by vaso and fragments thereof render these polypeptides or nucleic acids encoding these polypeptides useful for protecting the bone marrow of subjects treated with either chemotherapy or irradiation. For example, vaso or a fragment thereof is of use for treating subjects having tumors and cancers such as cervical cancer, breast cancer; melanoma, papilloma, liver cancer, prostate cancer, lung cancer, and nasopharyngeal carcinoma, or any neoplastic condition treated with irradiation or chemotherapy.

The method for stimulating proliferation of hematopoietic cells can also include administering variants of the 18 consecutive amino acids of SEQ ID NO:3, for example, sequences having at least 80%, 90%, 95%, or 98% sequence identity, and which retain the ability to stimulate hematopoiesis. Alternatively, the variant sequences can be included in longer peptides.

In view of the many possible embodiments to which the principles disclosed herein may be applied, it should be recognized that the illustrated embodiment is only a preferred example and should not be taken as a limitation on the scope of the invention. We therefore claim as our invention all that comes within the scope and spirit of these claims.

We claim:

1. An isolated peptide consisting of the amino acid sequence set forth as the twenty-seven consecutive amino acids from amino acid 120 to amino acid 146 of SEQ ID NO: 3.

2. An isolated peptide, wherein the peptide consists of one of the amino acid sequences set forth as amino acid 103 to amino acid 163 of SEQ ID NO: 3 (SEQ ID NO:4); amino acid 120 to amino acid 146 of SEQ ID NO: 3 (SEQ ID NO:5); amino acid 128 to amino acid 146 of SEQ ID NO: 3, (SEQ ID NO:6); amino acid 129 to amino acid 163 of SEQ ID NO: 3 (SEQ ID NO: 7); amino acid 120 to amino acid 150 of SEQ ID NO: 3, amino acid 100 to amino acid 160 of SEQ ID NO: 3, or amino acid 110 to amino acid 150 of SEQ ID NO: 3.

3. The isolated peptide of claim 2, wherein the peptide consists of the amino acid sequence set forth as SEQ ID NO:4, SEQ ID NO:5, SEQ ID NO:6 or SEQ ID NO:7.

4. An isolated fusion polypeptide comprising the peptide of claim 1 covalently linked to a carrier peptide.

5. The isolated fusion polypeptide of claim 4, wherein the carrier peptide is maltose binding protein, glutathione-S-transferase, or six consecutive histidine residues.

6. A composition comprising a therapeutically effective amount of the peptide of claim 1 and a pharmaceutically acceptable carrier.

7. The isolated polypeptide of claim 2, consisting of amino acid 128 to amino acid 146 of SEQ ID NO: 3 (SEQ ID NO:6).

8. The isolated polypeptide of claim 2, consisting of amino acid 129 to amino acid 163 of SEQ ID NO: 3 (SEQ ID NO: 7).

9. A composition comprising a therapeutically effective amount of the peptide of claim 3 and a pharmaceutically acceptable carrier.

10. A composition comprising a therapeutically effective amount of the peptide of claim 7 and a pharmaceutically acceptable carrier.

11. A composition comprising a therapeutically effective amount of the peptide of claim 8 and a pharmaceutically acceptable carrier.

12. An isolated fusion polypeptide comprising the peptide of claim 2, covalently linked to a carrier peptide.

13. The isolated fusion polypeptide of claim 12, wherein the carrier peptide is maltose binding protein, glutathione-S-transferase, or six consecutive histidine residues.

14. A composition comprising a therapeutically effective amount of the peptide of claim 2 and a pharmaceutically acceptable carrier.

15. An isolated fusion polypeptide comprising the peptide of claim 3, covalently linked to a carrier peptide.

16. The isolated fusion polypeptide of claim 15, wherein the carrier peptide is maltose binding protein, glutathione-S-transferase, or six consecutive histidine residues.

* * * * *